(12) United States Patent
Benigni et al.

(10) Patent No.: US 9,751,947 B2
(45) Date of Patent: Sep. 5, 2017

(54) ANTIBODIES AND DERIVATIVES THEREOF

(75) Inventors: Fabio Benigni, Rome (IT); Daniele D'Ambrosio, Allschwill (CH)

(73) Assignee: LAY LINE GENOMICS S.P.A., Rome (IT)

( * ) Notice: Subject to any disclaimer, the term of this patent is extended or adjusted under 35 U.S.C. 154(b) by 1092 days.

(21) Appl. No.: 12/866,184

(22) PCT Filed: Feb. 4, 2009

(86) PCT No.: PCT/EP2009/051285
§ 371 (c)(1),
(2), (4) Date: Nov. 5, 2010

(87) PCT Pub. No.: WO2009/098238
PCT Pub. Date: Aug. 13, 2009

(65) Prior Publication Data
US 2011/0145941 A1    Jun. 16, 2011

Related U.S. Application Data

(60) Provisional application No. 61/025,995, filed on Feb. 4, 2008.

(51) Int. Cl.
*C07K 16/00* (2006.01)
*C07K 16/28* (2006.01)
*A61K 39/00* (2006.01)

(52) U.S. Cl.
CPC .... *C07K 16/2863* (2013.01); *A61K 2039/505* (2013.01); *C07K 2317/52* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,624,821 | A | | 4/1997 | Winter et al. |
| 5,693,762 | A | * | 12/1997 | Queen et al. ............... 530/387.3 |
| 6,194,551 | B1 | | 2/2001 | Idusogie et al. |
| 6,491,916 | B1 | | 12/2002 | Bluestone et al. |

FOREIGN PATENT DOCUMENTS

| EP | 1181318 B2 | | 3/2012 |
| WO | 9845435 | | 10/1998 |
| WO | 0073344 | | 12/2000 |
| WO | 0178698 | | 10/2001 |
| WO | 2004032870 | | 4/2004 |
| WO | 2004096122 | | 11/2004 |
| WO | 2005000194 | | 6/2005 |
| WO | 2005061540 | | 7/2005 |
| WO | WO2005061540 a2 | * | 7/2005 |
| WO | 2005111077 | | 11/2005 |
| WO | 2006131951 | | 12/2006 |
| WO | 2006131952 | | 12/2006 |
| WO | 2006137106 | | 12/2006 |
| WO | 9721732 | | 6/2007 |
| WO | WO 2009098238 A1 | | 8/2009 |
| WO | 2009155932 | | 12/2009 |

OTHER PUBLICATIONS

Mariuzza et al. (Annu. Rev. Biophys. Biophys. Chem., 16: 139-159, 1987).*
Gussow et al (Methods in Enzymology, 203: 99-121, 1991).*
Winkler et al (J. Imm., 265:4505-4514, 2000).*
Rudikoff et al (Proc. Natl. Acad. Sci. USA 1982 vol. 79: p. 1979-1983).*
MacCallum et al. (J. Mol. Biol. 1996 Oct. 11; 262 (5): 732-745).*
Holm et al. (Mol. Immunol. Feb. 2007; 44 (6): 1075-1084).*
Dawbarn et al (Biochem. Soc. Trans. 34(4):587-590, 2006).*
Cattaneo et al.,"Functional Blockade of Tyrosine Kinase A in the Rat Basal Forebrain by a Novel Antagonistic Anti-Receptor Monoclonal Antibody," The Journal of Neuroscience, Nov. 15, 1999, 19(22):9687-9697.
International Search Report from International Application No. PCT/EP2009/0515285, dated May 4, 2009.
Ugolini et al., "The function neutralizing anti-TrkA antibody MNAC13 reduces inflammatory and neuropathic pain," PNAS, Feb. 20, 2007, vol. 104, No. 8, pp. 2985-2990.
Jones, P.T., et al., "Replacing the Complementarity-Determining Regions in a Human Antibody with those from a Mouse," Nature 321(6069):522-525, Nature Publishing Group, England (1986).
Kitamura, T., et al., "Establishment and Characterization of a Unique Human Cell Line That Proliferates Dependently on GM-CSF, IL-3, or Erythropoietin," Journal of Cellular Physiology 140(2):323-334, Alan R. Liss, Inc., United States (1989).
Riechmann, L., et al., "Reshaping Human Antibodies for Therapy," Nature 332(6162):323-327, Nature Publishing Group, United States (1988).
Verhoeyen, M., et al., "Reshaping human antibodies: grafting an antilysozyme activity,"Science 239(4847):1534-1536, American Association for the Advancement of Science, United States (1988).
Ward, E.S. and Ghetie, V., "The Effector Functions of Immunoglobins: Implications for Therapy," Therapeutic Immunology 2(2):77-94, Blackwell Science Ltd., England (1995).
International Preliminary Report on Patentability for International Patent Application No. PCT/EP2009/051285, International Bureau of WIPO, Geneva, Switzerland, issued Aug. 10, 2010.

(Continued)

*Primary Examiner* — Brad Duffy
(74) *Attorney, Agent, or Firm* — Sterne, Kessler, Goldstein & Fox P.L.L.C.

(57) ABSTRACT

An anti-TrkA antibody is provided that comprises:
a) a variable heavy chain comprising a sequence selected from any of BXhVH1, BXhVH2, BXhVH3, BXhVH4, BXhVH5, or HuVHWOv as shown in FIG. 1*a*; or from variants of any of said sequences
and/or
b) a variable light chain comprising a sequence selected from any of BXhVL1, BXhVL2, BXhVL3, BXhVL4, BXhVL5, BXhVL6, BXhVL7 or BXhVL8; as shown in FIG. 1*b*, or from variants of any of said sequences. TrkA-binding derivatives are also provided. Antibodies or derivatives of the present invention are useful in a number of therapies, including pain therapy.

20 Claims, 15 Drawing Sheets

(56) References Cited

OTHER PUBLICATIONS

Ahamed, J., et al., "C3a Enhances Nerve Growth Factor-Induced Nfat Activation and Chemokine Production in a Human Mast Cell Line, HMC-1," J Immunol 172(11):6961-6968, American Association of Immunologist, United States (2004).

Bennett, G.J. and Xie, Y.K., "A Peripheral Mononeuropathy in Rat that Produces Disorders of Pain Sensation like Those Seen in Man," Pain 33(1):87-107, Lippincott Williams & Wilkins, United States (1988).

Eddy, N. B., and Leimbach, D., "Synthetic Analgesics. II. Dithienylbutenyl- and Dithienylbutylamines," Journal of Pharmacology and Experimental Therapeutics 107(3):385-393, American Society for Pharmacology and Experimental Therapeutics, United States (1953).

McMahon, S.B., et al., "The Biological Effects of Endogenous Nerve Growth Factor on Adult Sensory Neurons Revealed By a trkA-IgG Fusion Molecule," Nature Medicine 1(8):774-780, Nature Publishing Company, United States (1995).

Porro, C.A. and Cavazzuti, M., "Spatial and Temporal Aspects of Spinal Cord and Brainstep Activation in the Formalin Paid Model," Prog Neurobiol. 41(5):565-607, Pergamon Press, England (1993).

U.S. Appl. No. 15/015,931, inventors Benigni, F., et al., filed on Feb. 4, 2016 (Not Published).

\* cited by examiner

Figure 1a

Sequence Alignment

Underlined, CDRs, as of EP1181318

HEAVY CHAIN:

```
mVHEP
EVKLMESGGGLVQPGSLKLSCAASGFTFSTYTMSWARQTPEKRLEWVAYISKGGGSTYYPDTVKGRFTISRDNAKNTLYLQMSSLKSEDTALYYCARGAMYGNDFFYPMDYWGQQTSVTVSS
(SEQ IN No. 15)
3-23*01    EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK...
(SEQ IN No. 19)
JH4
..YFDYWGQGTLVTVSS
(SEQ IN No. 20)
BXhVH1
EVQLLESGGGLVQPGGSLRLSCAASGFTFSTYTMSWVRQAPGKGLEWVSYISKGGGSTYYPDTVKGRFTISRDNSKNTLYLQMNSLRAEDTAVYYCAKGAMYGNDFFYPMDYWGQGTTVTVSS
(SEQ IN No. 1)
BXhVH2
EVKLLESGGGLVQPGGSLRLSCAASGFTFSTYTMSWVRQTPGKGLEWVAYISKGGGSTYYPDTVKGRFTISRDNSKNTLYLQMNSLRAEDTAVYYCAKGAMYGNDFFYPMDYWGQGTTVTVSS
(SEQ IN No. 2)
BXhVH3
EVQLLESGGGLVQPGGSLRLSCAASGFTFSTYIMSWVRQTPGKRLEWVAYISKGGGSTYYPDTVKGRFTISRDNSKNTLYLQMNSLRAEDTAVYYCAKGAMYGNDFFYPMDYWGQGTTVTVSS
(SEQ IN No. 3)
BXhVH4
EVQLLESGGGLVQPGGSLRLSCAASGFTFSTYTMSWVRQAPGKRLEWVAYISKGGGSTYYPDTVKGRFTISRDNSKNTLYLQMNSLRAEDTAVYYCARGAMYGNDFFYPMDYWGQGTTVTVSS
(SEQ IN No. 4)
BXhVH5
EVKLLESGGGLVQPGGSLRLSCAASGFTFSTYTMSWVRQTPGKRLEWVAYISKGGGSTYYPDTVKGRFTISRDNSKNTLYLQMNSLRAEDTAVYYCARGAMYGNDFFYPMDYWGQGTTVTVSS
(SEQ IN No. 5)
HuVHWO
EVQLLESGGGLVQPGGSLRLSCAASGFTFSTYTMSWARQAPGKGLEWVAYISKGGGSTYYPDTVKGRFTISRDNSKNTLYLQMNSLRAEDSAVYYCARGAMFGNDFFFPMDRWGQGTLVTVSS
(SEQ IN No. 17)
HuVHWov
EVQLLESGGGLVQPGGSLRLSCAASGFTFSTYTMSWARQAPGKGLEWVAYISKGGGSTYYPDTVKGRFTISRDNSKNTLYLQMNSLRAEDSAVYYCARGAMYGNDFFYPMDYWGQGTLVTVSS
(SEQ IN No. 6)
```

Figure 1b

LIGHT CHAIN:

```
mVLEP            DIVLSQSPAIMSASLGEEITLTCSASSSVSYMH-WYQQKSGTSPKLLIYTTTSNLASGVPSRFSGSGSGTFYSLTISSVEAEDAADYYCHQWSSYPWTFGGGTKLEIK
  (SEQ IN No. 16)
L6*01            EIVLTQSPATLSLSPGERATLSCRASQSVSSYLAWYQQKPGQAPRLLIYDASNRATGIPARFSGSGSGTDFTLTISSLEPEDFAVYYCQQRSNWP
  (SEQ IN No. 21)
JK1                                                                                                              ..WTFGQGTKVEIK
  (SEQ IN No. 22)
BXhVL1           EIVLTQSPATLSLSPGERATLSCSASSSVSYMH-WYQQKPGQAPRLLIYTTSNLASGIPARFSGSGSGTDFTLTISSLEPEDFAVYYCHQWSSYPWTFGQGTKLEIK
  (SEQ IN No. 7)
BXhVL2           BIVLTQSPATLSLSPGERATLSCSASSSVSYMH-WYQQKPGQSPRLLIYTTSNLASGIPSRFSGSGSGTDFTLTISSLEPEDAADYYCHQWSSYPWTFGQGTKLEIK
  (SEQ IN No. 8)
BXhVL3           QIVLTQSPATLSLSPGERATLSCSASSSVSYMH-WYQQKPGQSPRLLIYTTSNLASGIPSRFSGSGSGTFYTLTISSLEPEDFAVYYCHQWSSYPWTFGGGTKLEIK
  (SEQ IN No. 9)
BXhVL4           QIVLTQSPATLSLSPGERATLSCSASSSVSYMH-WYQQKPGQSPRLLIYTTSNLASGIPSRFSGSGSGTDFTLTISSLEPEDAADYYCHQWSSYPWTFGGGTKLEIK
  (SEQ IN No. 10)
BXhVL5           QIVLTQSPATLSLSPGERATLSCSASSSVSYMH-WYQQKPGQSPRLLIYTTSNLASGIPSRFSGSGSGTDYTLTISSLEPEDAADYYCHQWSSYPWTFGQGTKLEIK
  (SEQ IN No. 11)
BXhVL6           EIVLTQSPATLSLSPGEEATLSCSASSSVSYMH-WYQQKPGQSPRLLIYTTSNLASGIPSRFSGSGSGTFYTLTISSLEPEDAADYYCHQWSSYPWTFGGGTKLEIK
  (SEQ IN No. 12)
BXhVL7           QIVLTQSPATLSLSPGERATLSCSASSSVSYMH-WYQQKPGQSPRLLIYTTSNLASGIPSRFSGSGSGTFYTLTISSLEPEDAADYYCHQWSSYPWTFGGGTKLEIK
  (SEQ IN No. 13)
BXhVL8           QIVLTQSPATLSLSPGEEATLSCSASSSVSYMH-WYQQKSGTSPRLLIYTTSNLASGIPSRFSGSGSGTFYTLTISSLEPEDAADYYCHQWSSYPWTFGGGTKLEIK
  (SEQ IN No. 14)
HuVLW0           DIVLTQSPSSLSASVGDRVTITCSASSSVSYMH-WYQQKPGQAPKLLIYTTSNLASGVPSRFSGSGSGTDYTLTISSLQPEDVATYYCHQWSSYPWTFGGGTKVEIK
  (SEQ IN No. 18)
```

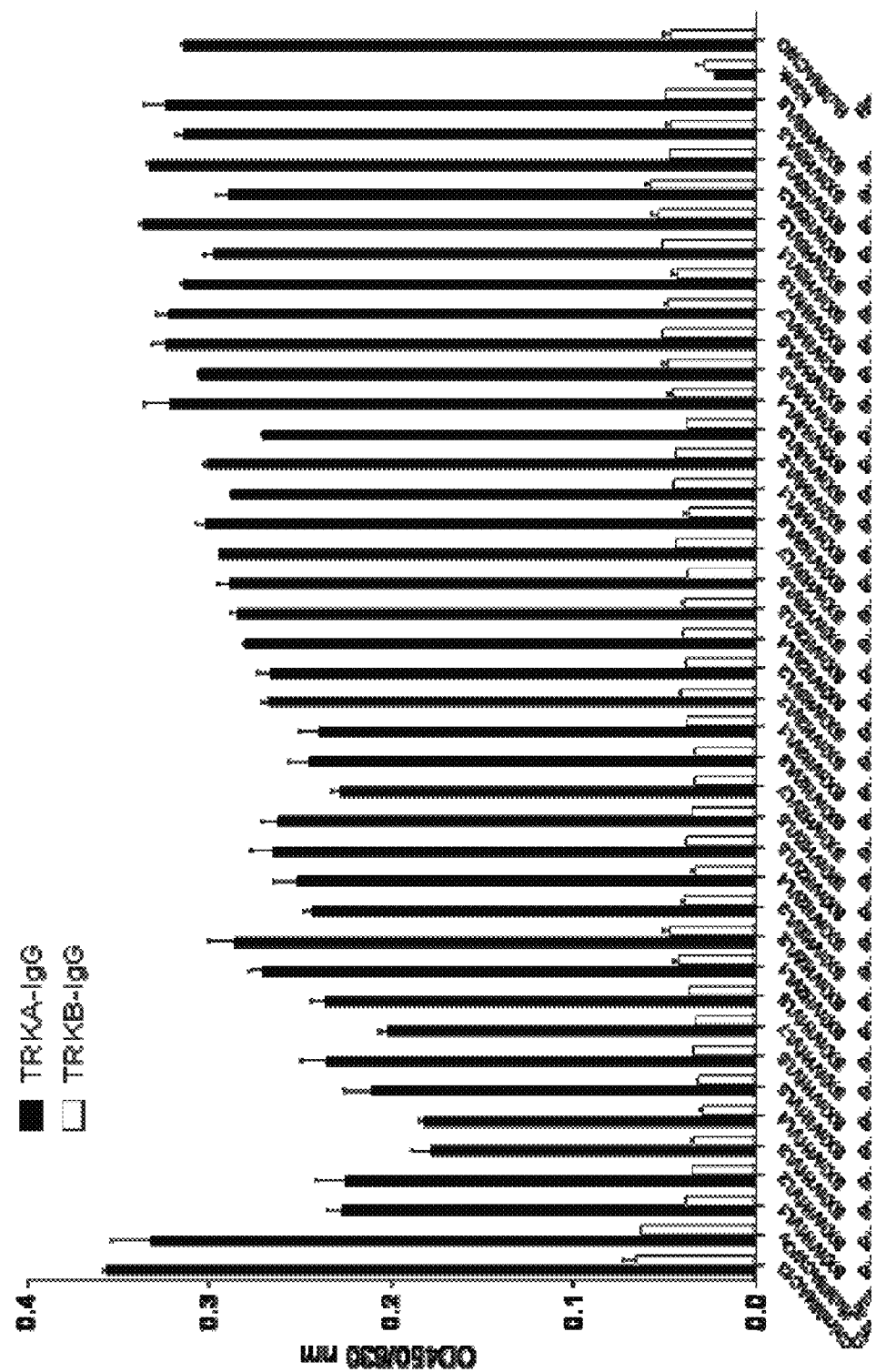

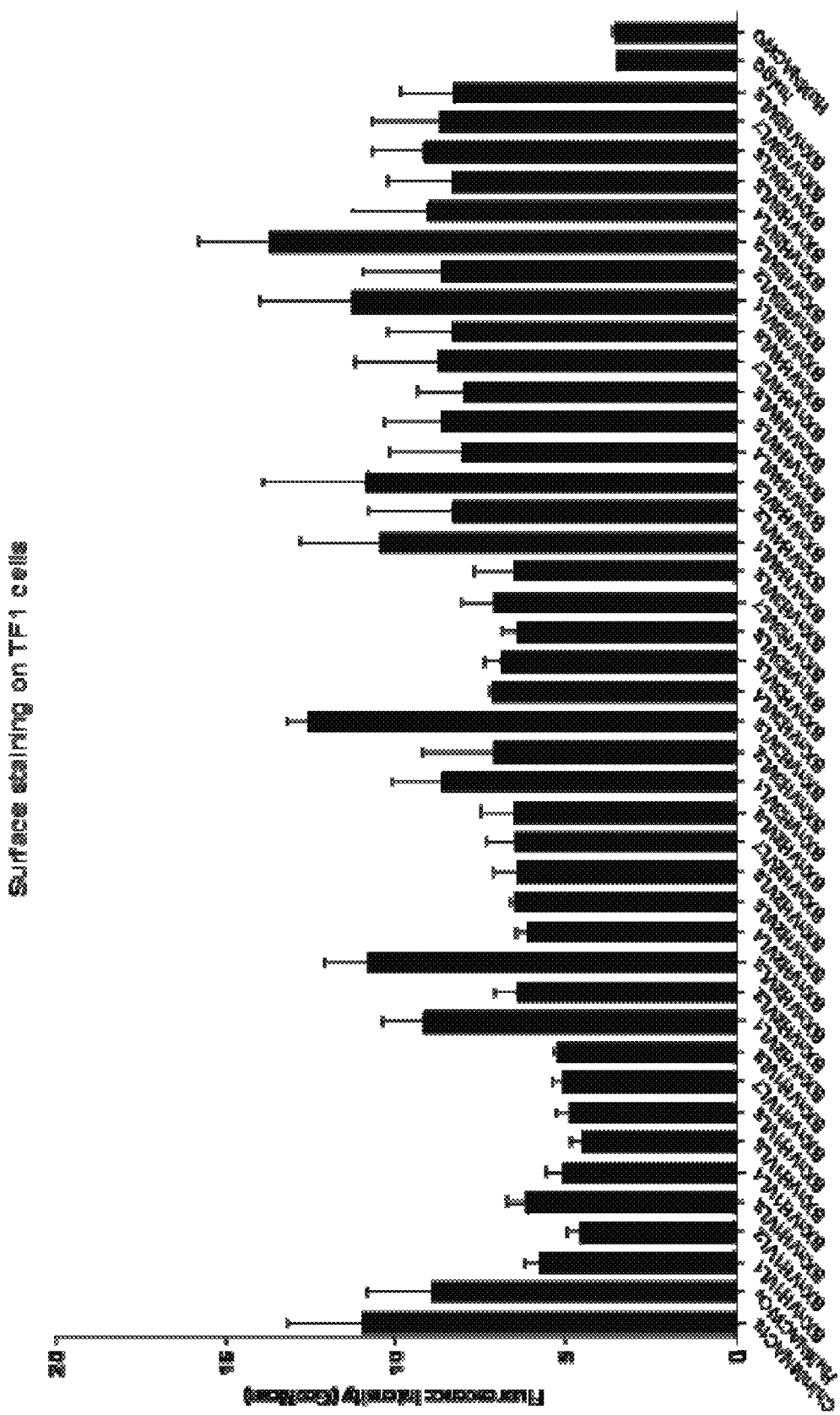

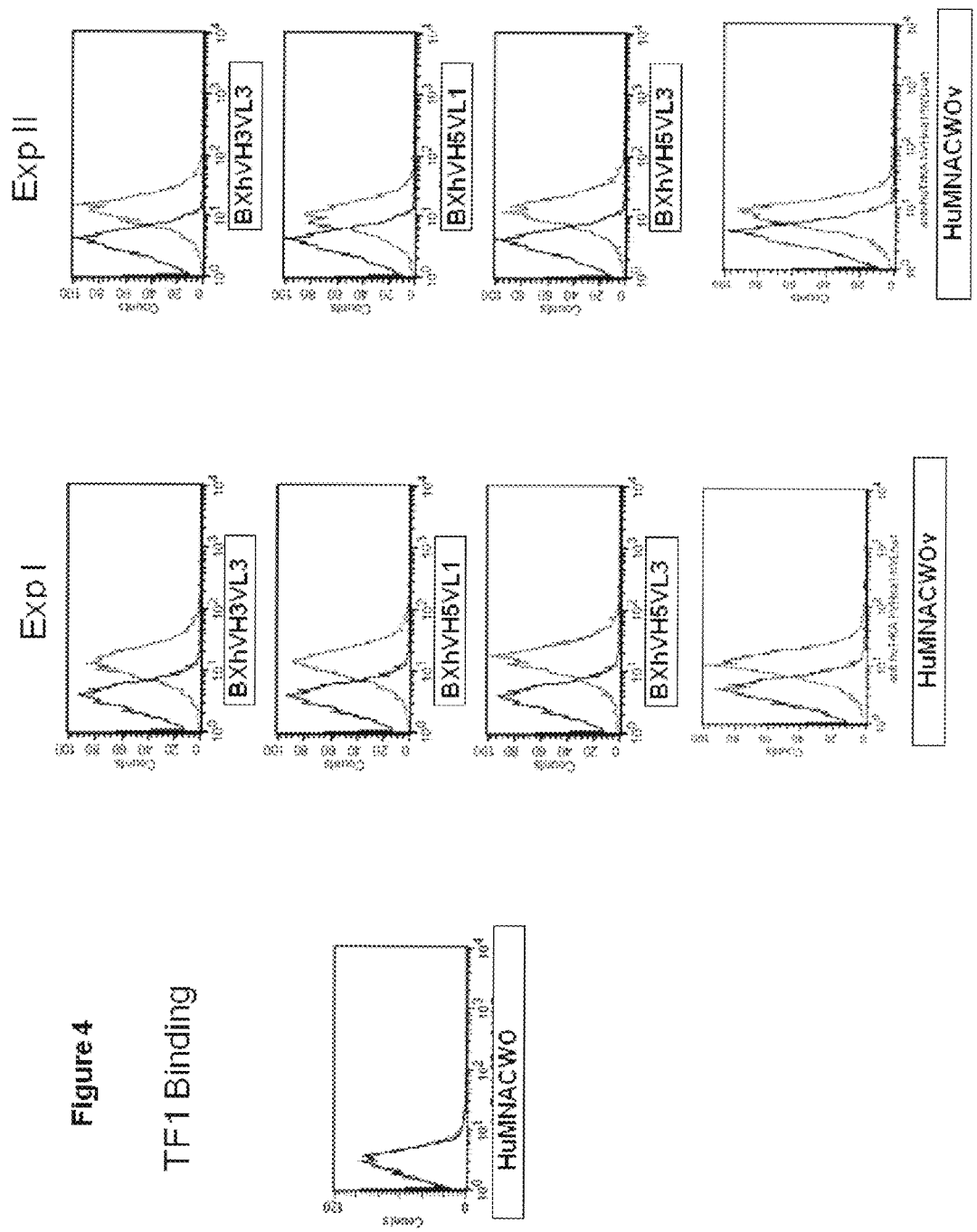

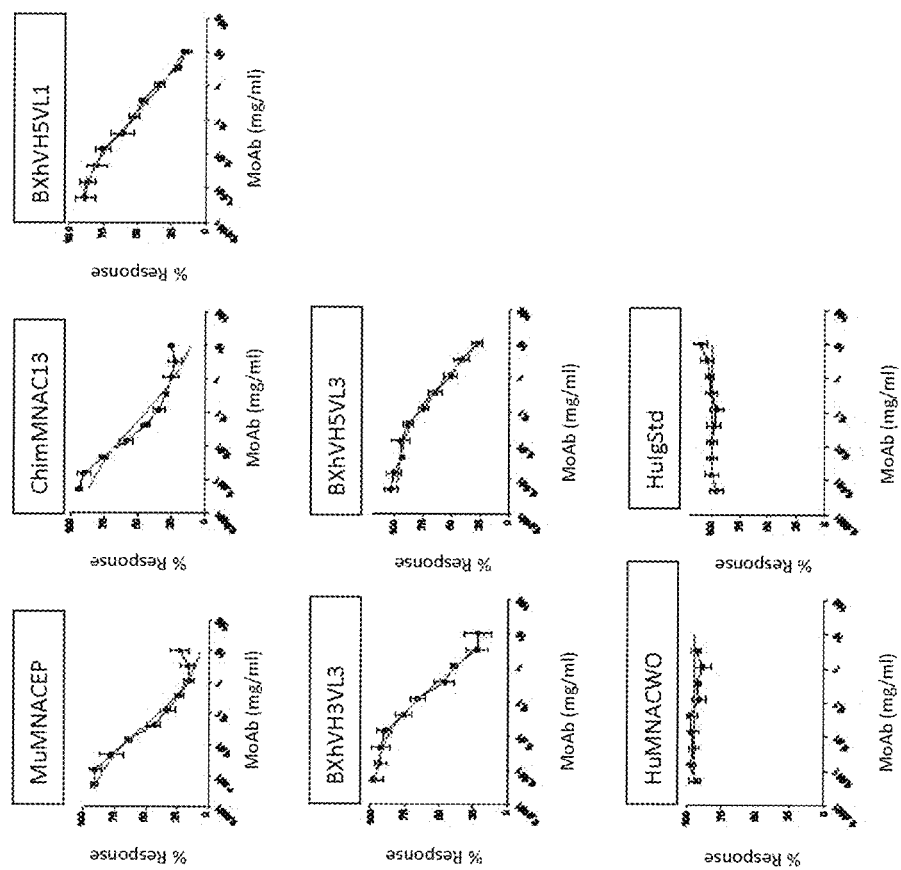

Figure 6

BXhVH5 heavy chain with constant region

EVKLLESGGGLVQPGGSLRLSCAASGFTFSTYTMSWVRQTPGK
RLEWVAYISKGGGSTYYPDTVKGRFTISRDNSKNTLYLQMNSLRA
EDTAVYYCARGAMYGNDFFYPMDYWGQGTTVTVSSASTKGPSV
FPLAPSSKSTSGGTAALGCLVKDYFPEPVTVSWNSGALTSGVHTF
PAVLQSSGLYSLSSVVTVPSSSLGTQTYICNVNHKPSNTKVDKKV
EPKSCDKTHTCPPCPAPELLGGPSVFLFPPKPKDTLMISRTPEVT
CVVVDVSHEDPEVKFNWYVDGVEVHNAKTKPREEQYNSTYRVV
SVLTVLHQDWLNGKEYKCKVSNKALPAPIEKTISKAKGQPREPQV
YTLPPSRDELTKNQVSLTCLVKGFYPSDIAVEWESNGQPENNYKT
TPPVLDSDGSFFLYSKLTVDKSRWQQGNVFSCSVMHEGLHNHYT
QKSLSLSPGK

BXhVL1 light chain with constant region

EIVLTQSPATLSLSPGERATLSCSASSSVSYMHWYQQKPGQAPRL
LIYTTSNLASGIPARFSGSGSGTDFTLTISSLEPEDFAVYYCHQWS
SYPWTFGQGTKLEIKRTVAAPSVFIFPPSDEQLKSGTASVVCLLN
NFYPREAKVQWKVDNALQSGNSQESVTEQDSKDSTYSLSSTLTL
SKADYEKHKVYACEVTHQGLSSPVTKSFNRGEC

Figure 7

BXhVH5 N297A heavy chain with constant region

EVKLLESGGGLVQPGGSLRLSCAASGFTFSTYTMSWVRQTPGKRLEWVAYISKGGGSTYYPDTV
KGRFTISRDNSKNTLYLQMNSLRAEDTAVYYCARGAMYGNDFYPMDYWGQGTTVTVSSASTKG
PSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYASTYRVVSVLTVLHQDWL
NGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEGLHNHYTQKSLS
LSPGK

Figure 11
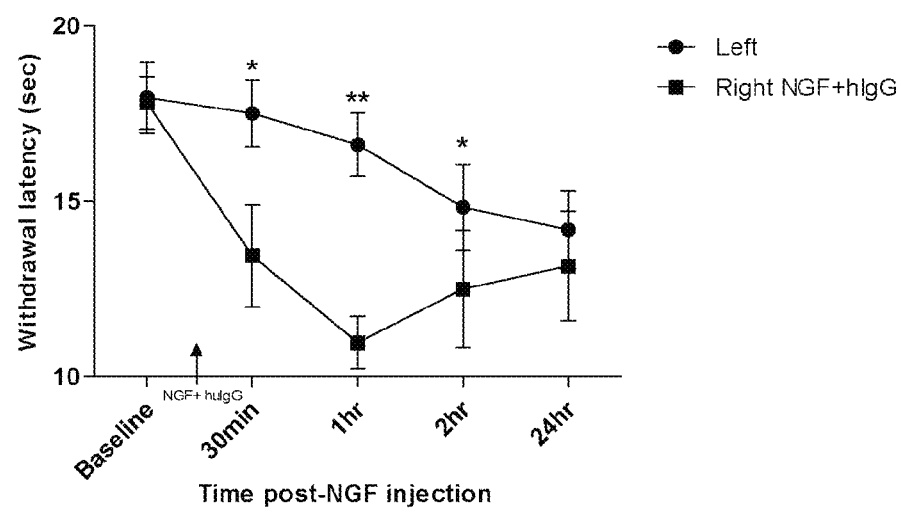
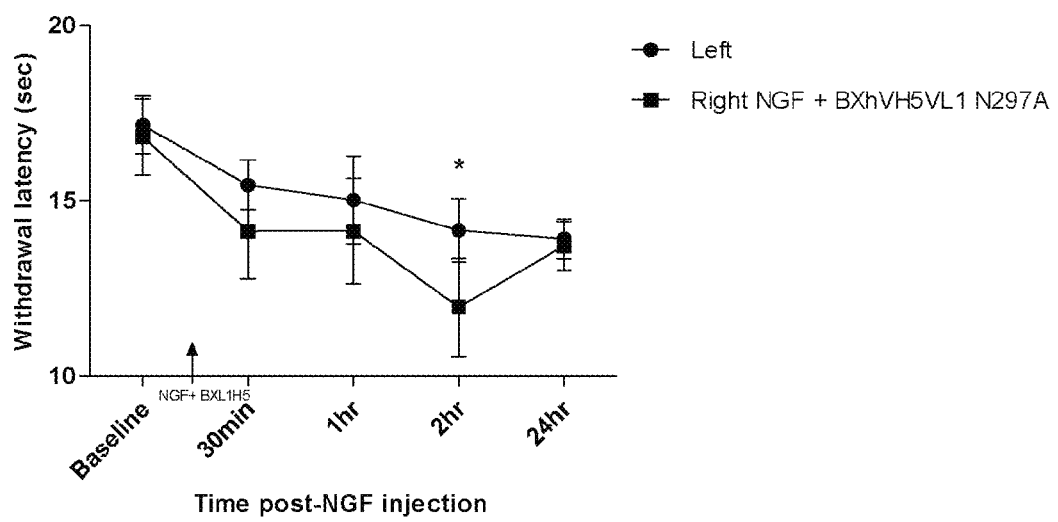

Figure 12
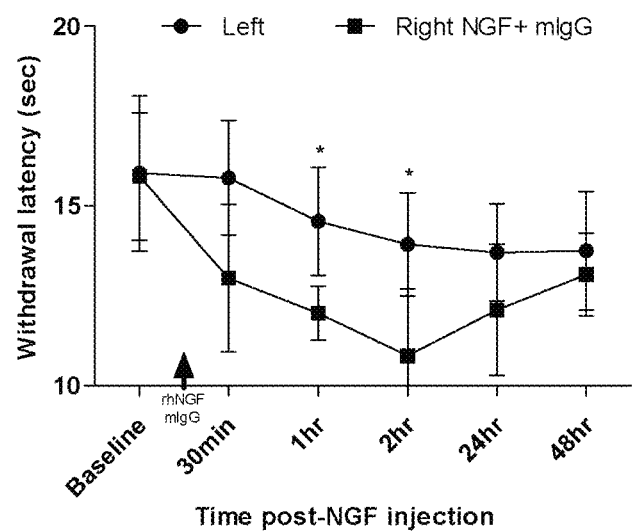
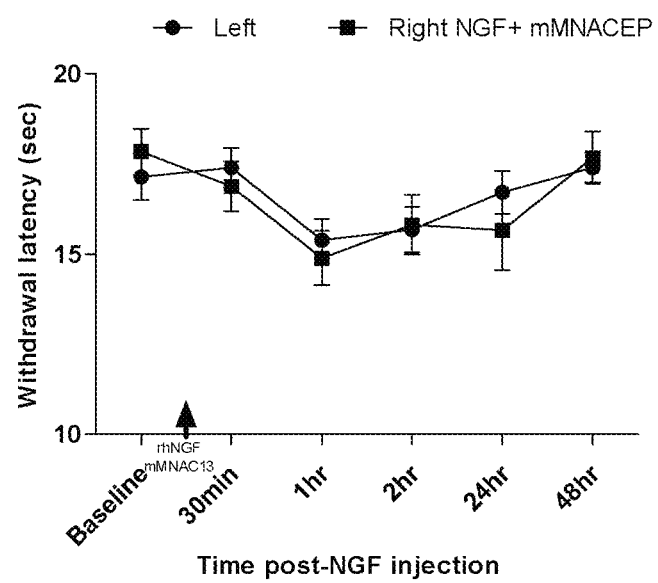

SEQUENCE LISTING

<160> NUMBER OF SEQ ID NOS: 23

<210> SEQ ID NO 1
<211> LENGTH: 123
<212> TYPE: PRT
<213> ORGANISM: Homo sapiens

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Ala Pro Gly Lys Gly Leu Glu Trp Val
        35                  40                  45

Ser Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Met Tyr Gly Asn Asp Phe Phe Tyr Pro Met Asp Tyr
            100                 105                 110

Trp Gly Gln Gly Thr Thr Val Thr Val Ser Ser
            115                 120
```

<210> SEQ ID NO 2
<211> LENGTH: 123
<212> TYPE: PRT
<213> ORGANISM: Homo sapiens

<400> SEQUENCE: 2

```
Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Thr Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Met Tyr Gly Asn Asp Phe Phe Tyr Pro Met Asp Tyr
            100                 105                 110

Trp Gly Gln Gly Thr Thr Val Thr Val Ser Ser
            115                 120
```

<210> SEQ ID NO 3
<211> LENGTH: 123
<212> TYPE: PRT
<213> ORGANISM: Homo sapiens

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Thr Met Ser Trp Val Arg Gln Thr Pro Gly Lys Arg Leu Glu Trp Val
            35                  40                  45

Ala Tyr Ile Ser Lys Gly Gly Ser Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Met Tyr Gly Asn Asp Phe Phe Tyr Pro Met Asp Tyr
                100                 105                 110

Trp Gly Gln Gly Thr Thr Val Thr Val Ser Ser
            115                 120
```

<210> SEQ ID NO 4
<211> LENGTH: 123
<212> TYPE: PRT
<213> ORGANISM: Homo sapiens

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Thr Met Ser Trp Val Arg Gln Ala Pro Gly Lys Arg Leu Glu Trp Val
            35                  40                  45

Ala Tyr Ile Ser Lys Gly Gly Ser Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Met Tyr Gly Asn Asp Phe Phe Tyr Pro Met Asp Tyr
                100                 105                 110

Trp Gly Gln Gly Thr Thr Val Thr Val Ser Ser
            115                 120
```

<210> SEQ ID NO 5
<211> LENGTH: 123
<212> TYPE: PRT
<213> ORGANISM: Homo sapiens

<400> SEQUENCE: 5

```
Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Thr Met Ser Trp Val Arg Gln Thr Pro Gly Lys Arg Leu Glu Trp Val
            35                  40                  45

Ala Tyr Ile Ser Lys Gly Gly Ser Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Met Tyr Gly Asn Asp Phe Phe Tyr Pro Met Asp Tyr
                100                 105                 110
```

```
Trp Gly Gln Gly Thr Thr Val Thr Val Ser Ser
            115                 120

<210> SEQ ID NO 6
<211> LENGTH: 123
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Thr Met Ser Trp Ala Arg Gln Ala Pro Gly Lys Gly Leu Glu Trp Val
        35                  40                  45
Ala Tyr Ile Ser Lys Gly Gly Ser Thr Tyr Tyr Pro Asp Thr Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Ser Ala Val Tyr Tyr Cys
                85                  90                  95
Ala Arg Gly Ala Met Tyr Gly Asn Asp Phe Phe Tyr Pro Met Asp Tyr
            100                 105                 110
Trp Gly Gln Gly Thr Leu Val Thr Val Ser Ser
            115                 120

<210> SEQ ID NO 7
<211> LENGTH: 106
<212> TYPE: PRT
<213> ORGANISM: Homo sapiens

<400> SEQUENCE: 7

Glu Ile Val Leu Thr Gln Ser Pro Ala Thr Leu Ser Leu Ser Pro Gly
1               5                   10                  15
Glu Arg Ala Thr Leu Ser Cys Ser Ala Ser Ser Ser Val Ser Tyr Met
            20                  25                  30
His Trp Tyr Gln Gln Lys Pro Gly Gln Ala Pro Arg Leu Leu Ile Tyr
            35                  40                  45
Thr Thr Ser Asn Leu Ala Ser Gly Ile Pro Ala Arg Phe Ser Gly Ser
        50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys His Gln Trp Ser Ser Tyr Pro Trp Thr
                85                  90                  95
Phe Gly Gln Gly Thr Lys Leu Glu Ile Lys
            100                 105

<210> SEQ ID NO 8
<211> LENGTH: 106
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15
Glu Arg Ala Thr Leu Ser Cys Ser Ala Ser Ser Ser Val Ser Tyr Met
            20                  25                  30
```

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Ala Ala Asp Tyr Tyr Cys His Gln Trp Ser Ser Tyr Pro Trp Thr
                 85                  90                  95

Phe Gly Gln Gly Thr Lys Leu Glu Ile Lys
            100                 105

<210> SEQ ID NO 9
<211> LENGTH: 106
<212> TYPE: PRT
<213> ORGANISM: Homo sapiens

<400> SEQUENCE: 9

Gln Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Tyr Met
                 20                  25                  30

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
 50                  55                  60

Gly Ser Gly Thr Phe Tyr Thr Leu Thr Ile Ser Ser Leu Glu Pro Glu
 65                  70                  75                  80

Asp Phe Ala Val Tyr Tyr Cys His Gln Trp Ser Ser Tyr Pro Trp Thr
                 85                  90                  95

Phe Gly Gly Gly Thr Lys Leu Glu Ile Lys
            100                 105

<210> SEQ ID NO 10
<211> LENGTH: 106
<212> TYPE: PRT
<213> ORGANISM: Homo sapiens

<400> SEQUENCE: 10

Gln Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Tyr Met
                 20                  25                  30

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Ala Ala Asp Tyr Tyr Cys His Gln Trp Ser Ser Tyr Pro Trp Thr
                 85                  90                  95

Phe Gly Gly Gly Thr Lys Leu Glu Ile Lys
            100                 105

<210> SEQ ID NO 11
<211> LENGTH: 106
<212> TYPE: PRT
<213> ORGANISM: Homo sapiens

<400> SEQUENCE: 11

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
                20                  25                  30

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Ala Ala Asp Tyr Tyr Cys His Gln Trp Ser Ser Tyr Pro Trp Thr
                85                  90                  95

Phe Gly Gln Gly Thr Lys Leu Glu Ile Lys
            100                 105

<210> SEQ ID NO 12
<211> LENGTH: 106
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Glu Ala Thr Leu Ser Cys Ser Ala Ser Ser Ser Val Ser Tyr Met
                20                  25                  30

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
        50                  55                  60

Gly Ser Gly Thr Phe Tyr Thr Leu Thr Ile Ser Ser Leu Glu Pro Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105

<210> SEQ ID NO 13
<211> LENGTH: 106
<212> TYPE: PRT
<213> ORGANISM: Homo sapiens

<400> SEQUENCE: 13

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
                20                  25                  30

His Trp Tyr Gln Gln Lys Pro Gly Gln Ser Pro Arg Leu Leu Ile Tyr
            35                  40                  45

Thr Thr Ser Asn Leu Ala Ser Gly Ile Pro Ser Arg Phe Ser Gly Ser
        50                  55                  60

Gly Ser Gly Thr Phe Tyr Thr Leu Thr Ile Ser Ser Leu Glu Pro Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys

<210> SEQ ID NO 14
<211> LENGTH: 106
<212> TYPE: PRT
<213> ORGANISM: Homo sapiens

<400> SEQUENCE: 14

Gln Ile Val Leu Thr Gln Ser Pro Ala Thr Leu Ser Leu Ser Pro Gly
1               5                   10                  15

Glu Glu Ala Thr Leu Ser Cys Ser Ala Ser Ser Ser Val Ser Tyr Met
            20                  25                  30

His Trp Tyr Gln Gln Lys Ser Gly Thr Ser Pro Arg Leu Leu Ile Tyr
        35                  40                  45

Thr Thr Ser Asn Leu Ala Ser Gly Ile Pro Ser Arg Phe Ser Gly Ser
    50                  55                  60

Gly Ser Gly Thr Phe Tyr Thr Leu Thr Ile Ser Ser Leu Glu Pro Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105

<210> SEQ ID NO 15
<211> LENGTH: 123
<212> TYPE: PRT
<213> ORGANISM: Mus musculus

<400> SEQUENCE: 15

Glu Val Lys Leu Met Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Ala Arg Gln Thr Pro Glu Lys Arg Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Gly Ala Met Tyr Gly Asn Asp Phe Phe Tyr Pro Met Asp Tyr
            100                 105                 110

Trp Gly Gln Gln Thr Ser Val Thr Val Ser Ser
        115                 120

<210> SEQ ID NO 16
<211> LENGTH: 106
<212> TYPE: PRT
<213> ORGANISM: Mus musculus

<400> SEQUENCE: 16

Asp Ile Val Leu Ser Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Leu Leu Ile Thr
        35                  40                  45

Thr Thr Ser Asn Leu Ala Ser Gly Val Pro Ser Arg Phe Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
                100                 105

<210> SEQ ID NO 17
<211> LENGTH: 123
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Thr Met Ser Trp Ala Arg Gln Ala Pro Gly Lys Gly Leu Glu Trp Val
            35                  40                  45

Ala Tyr Ile Ser Lys Gly Gly Ser Thr Tyr Tyr Pro Asp Thr Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Pro Met Asp Arg
                100                 105                 110

Trp Gly Gln Gly Thr Leu Val Thr Val Ser Ser
            115                 120

<210> SEQ ID NO 18
<211> LENGTH: 106
<212> TYPE: PRT
<213> ORGANISM: Homo sapiens

<400> SEQUENCE: 18

Asp Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

His Trp Tyr Gln Gln Lys Pro Gly Gln Ala Pro Lys Leu Leu Ile Tyr
            35                  40                  45

Thr Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Val Ala Thr Tyr Tyr Cys His Gln Trp Ser Ser Tyr Pro Trp Thr
                85                  90                  95

Phe Gly Gly Gly Thr Lys Val Glu Ile Lys
                100                 105

<210> SEQ ID NO 19
<211> LENGTH: 98
<212> TYPE: PRT
<213> ORGANISM: Homo sapiens -continued

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 20
<211> LENGTH: 15
<212> TYPE: PRT
<213> ORGANISM: Homo sapiens

<400> SEQUENCE: 20

Tyr Phe Asp Tyr Trp Gly Gln Gly Thr Leu Val Thr Val Ser Ser
1               5                   10                  15

<210> SEQ ID NO 21
<211> LENGTH: 95
<212> TYPE: PRT
<213> ORGANISM: Homo sapiens

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 22
<211> LENGTH: 12
<212> TYPE: PRT
<213> ORGANISM: Homo sapiens

<400> SEQUENCE: 22

Trp Thr Phe Gly Gln Gly Thr Lys Val Glu Ile Lys
1               5                   10

<210> SEQ ID NO 23
<211> LENGTH: 453
<212> TYPE: PRT
<213> ORGANISM: Homo sapiens

<400> SEQUENCE: 23

-continued

```
Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Thr Pro Gly Lys Arg Leu Glu Trp Val
        35                  40                  45

Ala Tyr Ile Ser Lys Gly Gly Ser Thr Tyr Tyr Pro Asp Thr Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Met Tyr Gly Asn Asp Phe Phe Tyr Pro Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
```

-continued

```
            420                 425                 430
Val Met His Glu Gly Leu His Asn His Tyr Thr Gln Lys Ser Leu Ser
            435                 440                 445
Leu Ser Pro Gly Lys
    450
```

ANTIBODIES AND DERIVATIVES THEREOF

CROSS-REFERENCE TO RELATED APPLICATIONS

This application claims the benefit of U.S. Provisional Application No. 61/025,995, filed Feb. 4, 2008, and International Patent Application No. PCT/EP2009/051285, filed Feb. 4, 2009, the disclosures of which are herein incorporated by reference in their entirety.

FIELD

The present invention relates to antibodies and to derivatives thereof, especially to humanised antibodies and derivatives thereof.

BACKGROUND

Nerve growth factor (NGF) acts through two membrane receptors. One is the relatively low affinity p75 receptor. The other is a 140 KDa high affinity receptor, known as TrkA.

NGF has potential use in the treatment of a wide range of disorders, such as various neurodegenerative disorders (including Alzheimer's disease), diabetes and leprosy.

However NGF can have various undesired agonist properties. These include an increase in pain sensitivity. The NGF-TrkA system provides a potential target for therapies for pain.

Various anti-TrkA antibodies have been produced. One such antibody is a monoclonal antibody which is referred to as 5C3 in WO 97/21732 (McGill University). However, this was found to be a TrkA agonist and is therefore not useful for reducing pain. Specifically, when binding to TrkA this antibody does not prevent the functional activation thereof.

An anti-TrkA monoclonal antibody known as MNAC13 is disclosed in WO 00/73344 (Societa Italiana Per La Ricerca Scientifica), from which EP-B-118138 (Lay Line Genomics SpA) is derived. This antibody and various derivatives thereof are said to be effective in preventing the functional activation of TrkA in a range of biological systems. The MNAC13 monoclonal antibody was used in a standard nociception test and was found to provide remarkable hypoalgesia.

A single chain Fv (ScFv) variant of this antibody is also disclosed in WO 00/73344 and is referred to therein as MNAC13 ScFv. This contains the variable light and heavy chain regions of the larger antibody linked together by a linker polypeptide, which joins the C-terminus of the VL region with the N-terminus of the VII region. This variant was found to bind TrkA as efficiently as MNAC13. The sequence of the light and heavy variable regions was compared with that of the corresponding regions of the antibody described in WO 97/21732 and it was found that there was only a low level of overall sequence identity therewith.

WO 06/131952 (Lay Line Genomics SpA) discloses medical uses of anti-TrkA antibodies in treating chronic pain. It provides evidence of this by using models of persistent pain, in particular the Chronic Constriction Injury (CCI) model.

WO 06/137106 (Lay Line Genomics SpA) discloses using an anti-TrkA antibody capable of inhibiting the binding between NGF and TrkA in combination with at least one opioid analgesic for treating or preventing pain. It is explained that this combination therapy allows a reduced opioid dosage to provide the same level of pain relief as a much higher dosage. This can therefore be useful in reducing the level of opioid side effects in pain therapy, because dosages can be lowered.

WO 05/061540 (Lay Line Genomics SpA & Scuolo Internazionale Superiore Di Studi Avanzati-Sissa) discloses a method of humanisation of antibodies in which structural data obtained from crystallographic studies are used to conduct the first design stages of humanisation. As examples, WO 05/061540 takes anti-TrkA antibodies, as disclosed in WO 00/73344, and anti-NGF antibodies as starting points, and then redesigns them using the disclosed method.

Whilst the humanised antibodies disclosed in WO 05/061540 are useful, there is a need to provide additional humanised antibodies so as to expand the possibilities for effective therapies.

DETAILED DESCRIPTION

The present inventors have now provided a range of anti-TrkA antibodies and derivatives thereof that are not disclosed in WO 05/061540. The inventors have also provided data indicating the utility of such antibodies. Prior to the present invention these antibodies were simply not known in the art and the data provided could not have been predicted.

According to one aspect of the present invention, there is provided an anti-TrkA antibody that comprises:

a) a variable heavy chain comprising a sequence selected from any of BXhVH1 (SEQ ID NO 1), BXhVH2 (SEQ ID NO 2), BXhVH3 (SEQ ID NO 3), BXhVH4 (SEQ ID NO 4), BXhVH5 (SEQ ID NO 5), or HuVHWOv (SEQ ID NO 6), as shown in FIG. 1a; or from variants of any of said sequences;

and/or b) a variable light chain comprising a sequence selected from any of BXhVL1 (SEQ ID NO 7), BXhVL2 (SEQ ID NO 8), BXhVL3 (SEQ ID NO 9), BXhVL4 (SEQ ID NO 10), BXhVL5 (SEQ ID NO 11), BXhVL6 (SEQ ID NO 12), BXhVL7 (SEQ ID NO 13) or BXhVL8 (SEQ ID NO 14); as shown in FIG. 1b, or from variants of any of said sequences.

A derivative of said antibody is also provided; wherein the derivative is capable of binding TrkA.

More preferably, the antibody comprises both a variable heavy chain as described in a) above and a variable light chain as described in part b), i.e. it comprises one of the following combinations of light and heavy chains:

```
BXhVH1VL1, BXhVH1VL2, BXhVH1VL3, BXhVH1VL4,
BXhVH1VL5, BXhVH1VL6, BXhVH1VL7, BXhVH1VL8,

BXhVH2VL1, BXhVH2VL2, BXhVH2VL3, BXhVH2VL4,
BXhVH2VL5, BXhVH2VL6, BXhVH2VL7, BXhVH2VL8,

BXhVH3VL1, BXhVH3VL2, BXhVH3VL3, BXhVH3VL4,
BXhVH3VL5, BXhVH3VL6, BXhVH3VL7, BXhVH3VL8,

BXhVH4VL1, BXhVH4VL2, BXhVH4VL3, BXhVH4VL4,
BXhVH4VL5, BXhVH4VL6, BXhVH4VL7, BXhVH4VL8,

BXhVH5VL1, BXhVH5VL2, BXhVH5VL3, BXhVH5VL4,
BXhVH5VL5, BXhVH5VL6, BXhVH5VL7, BXhVH5VL8,
or

HuVHWOv/HuVLWO.
```

Desirably, the derivative of the antibody has at least one CDR region selected from the regions underlined in FIGS. 1a & 1b for each sequence, or from variants thereof having no more than two amino acid changes (preferably no more than one amino acid change) per underlined region.

More desirably, it has a plurality of CDR regions selected from the regions underlined in FIGS. 1a & 1b for each sequence, or from variants thereof having no more than two amino acid changes (preferably no more than one amino acid change) per underlined region.

It may therefore comprise one, two, three, four, five or six of such CDR regions (optionally in combination with one or more other CDR regions).

It may preferably comprise at least the third CDR region of the heavy chain, more preferably at least the third CDR region of the heavy and light chains.

Most desirably, however, it has six CDR regions corresponding to the six CDR regions underlined in FIGS. 1a & 1b for each sequence or corresponding to variants thereof having no more than two amino acid changes per underlined region.

Indeed, in most cases, it is preferred that few or no changes are made to the CDR sequences. Thus one, two, three, four, five, or even all six CDR regions may have the same amino acid sequences as those shown in FIGS. 1a & 1b.

Turning now to framework regions, it is preferred that the derivative has at least one framework region selected from the non-underlined sequences shown in FIGS. 1a & 1b or from variants thereof that have at least 75% amino acid sequence identity therewith (e.g. at least 80%, at least 85%, at least 90%, at least 95% or at least 98% sequence identity therewith).

The degree of amino acid sequence identity can be determined by simple alignments of the sequences without any gaps and determining the sequence differences.

Sequences can be aligned according to Kabat's numbering scheme and sequence identities can then be determined accordingly (See Kabat, Sequences of Proteins of Immunological Interest, National Institutes of Health, Bethesda Md., 1987 & 1991). This numbering scheme is discussed in WO 05/061540 (Reference can also be made to Chothia & Lesk, J. Mol. Biol., 196, 901 (1987) and to Chothia et al., Nature, 342, 878 (1989)).

Less preferably, one or more gaps may be allowed (e.g. for one or more amino acid insertions/deletions) and gap penalties may then be assigned.

Sequence identity can be determined using sequence analysis software e.g., BLASTN or BLASTP (available at www.ncbi.nlm.nih.gov/BLAST/). The default parameters for comparing two sequences (e.g. "Blast"ing two sequences against each other) by BLASTN (for nucleotide sequences) are reward for match=1, penalty for mismatch=2, open gap=5, extension gap=2. When using BLASTP for protein sequences, the default parameters are reward for match=0, penalty for mismatch=0, open gap=11, and extension gap=1].

More preferably, a plurality of framework regions is present and these regions are selected from the non-underlined sequences shown in FIGS. 1a & 1b or from variants thereof that have at least 75% amino acid sequence identity therewith (e.g. at least 80%, at least 85%, at least 90%, at least 95% or at least 98% sequence identity.

Each chain shown in FIGS. 1a & 1b has four framework regions. Thus it is preferred that at least two, at least three or four such regions/variants thereof are present.

Most preferably, all four framework regions or variants thereof are present.

Where one or more variant framework regions are present, it is generally preferred that the these regions do not include amino acid substitutions that would result in a change to an amino acid that is present in a murine sequence at the corresponding position.

The relevant murine amino acids that can be used for comparison are shown in mVHEP and mVLEP in FIGS. 1a & 1b respectively, with the exception that, for the purposes of this discussion, the few italicised amino acids shown in mVHEP and mVLEP are considered to be non-murine. At these positions the residues considered to be murine are given in the table below, in the order in which the italicised residues appear in the Figures.

| Position | Italicised residue shown in Figure | Corresponding murine residue |
|---|---|---|
| Heavy chain | M | V |
| Heavy chain | Q | G |
| Light Chain | D | Q |
| Light Chain | S | T |

Thus the percentage of humanisation of one or more framework regions may be reduced by amino acids substitutions that do not necessarily increase the percentage of murine residues present.

These may result from conservative non-murine amino acid substitutions and/or from non-conservative non-murine substitutions.

However conservative substitutions are most preferred.

Amino acids can be grouped as follows:
Group I (hydrophobic lateral chains): M, A, V, L, I;
Group II (neutral hydrophilic lateral chains): C, S, T, N, Q;
Group III (acid lateral chains): D, E;
Group IV (basic lateral chains): K, R;
Group V (residues that influence the orientation of the main chain): G, P; and
Group VI (aromatic lateral chains): F, Y, W.

Conservative amino acid substitutions entail substitutions between amino acid of the same group, whilst non conservative amino acid substitutions entail an exchange between members of different groups.

Whatever sequences are present in the different regions of the light and/or heavy chains, it is preferred that an antibody or derivative of the present invention has certain functional characteristics.

In addition to binding to TrkA, it is preferred that an antibody or derivative of the present invention is capable of blocking or reducing the binding of NGF to TrkA.

Preferably, it is capable of blocking or reducing one or more biological activities that would otherwise be induced by the binding of NGF to the TrkA receptor.

Thus it is preferred that it is an antagonist of one or more activities induced by NGF binding to TrkA (rather than an agonist). Thus the antibodies and derivatives thereof according to the invention suitably prevent the functional activation of TrkA. Inhibition of functional activation of TrkA by antibodies and derivatives thereof can lead to analgesia in vivo.

Various assay procedures can be used.

A standard assay is the classical PC12 in vitro assay in which PC12 cells are incubated with NGF and candidates are assessed to see if they are effective in reducing the extension of NGF-induced neuritic growth. This model was used in WO 00/73344, for example.

In another assay, preferred antibodies produce an OD450/630 nm value of greater than 0.1 in the TrkA-IgG binding assay illustrated by FIG. 2. More preferably the OD450/630 nm value is greater than 0.2. Most preferably it is greater than 0.3.

In a further assay, preferred antibodies or derivatives thereof provide an increase in FACS staining of TF1 cells in the FACS based assay described in the Examples (see Table 2). This is preferably an increase of over 1.0 fold. More preferably it is an increase that is at least 1.5 fold, at least 2.0 fold or at least 2.5 fold. Most preferably it is at least 3.0 fold.

Additional assays include assays for pain reduction, as described later in connection with the medical uses of the present invention (It is particularly desirable for medical applications that the antibodies/derivatives thereof act as antagonists rather than agonists in respect of the pain response).

Desired antibodies/derivatives of the present invention are selective in that they bind with greater affinity to TrkA than to TrkB (Compare the black and white columns in FIG. 2, for example).

For example they preferably have a binding affinity that is at least 2 times, at least 4 times, or at least 6 times as great for TrkA than for TrkB.

High binding affinities to TrkA relative to TrkB result in greater selectivity and a lower risk of undesired side effects.

Binding affinities can be readily assayed by comparative binding studies, such as those illustrated in FIG. 2.

Turning now to highly preferred antibodies of the present invention, these comprise one of the following combinations of light and heavy chains: BXhVH3VL3, BXhVH5VL1 or BXhVH5VL3.

These gave the best results in the assay illustrated by FIG. 3.

Preferred derivatives are derivatives of BXhVH3VL3, BXhVH5VL1 or BXhVH5VL3.

It will be appreciated from the foregoing discussion that a wide range of antibodies and derivatives thereof are within the scope of the present invention.

These have numerous applications, including those discussed below:

Medical Applications

Antibodies or derivatives of the present invention can be used in medicine.

They can be used to treat various disorders/conditions, as set out in various categories below.

The invention thus provides a method of treatment of the below mentioned conditions which comprises administering to a subject, suitably a mammalian subject especially a human subject, in need thereof a therapeutically effective amount of an antibody or derivative as described herein such that the condition is thereby treated.

The invention also provides use of an antibody or derivative as described herein in the manufacture of a medicament for the treatment of the below mentioned conditions.

The invention also provides a kit of parts comprising an antibody or derivative as described herein together with instructions directing the use thereof by a subject for the treatment of the below mentioned conditions.

Here the term "treatment" includes therapeutic treatment of an existing disorder/condition. It also includes prophylactic treatment. It further includes the amelioration of one or more adverse symptoms, even if a patient is not cured of a given disorder/condition. For example, pain may be alleviated or reduced.

Pain

A preferred medical use is in the treatment of pain.

According to International Association for the Study of Pain ("IASP") pain is generally defined as "An unpleasant sensory and emotional experience associated with actual or potential tissue damage, or described in terms of such damage or both". The essential element in all forms of pain is the activation of specialized high-threshold receptors and nerve fibers to warn the organism of potential tissue damage. The involvement of inflammatory cells and processes is a common element in many pain states. The term "acute pain" means immediate, generally high threshold, pain brought about by injury such as a cut, crush, burn, or by chemical stimulation. The term "chronic pain," as used herein, means pain other than acute pain, both of inflammatory and neuropathic origin. It is understood that chronic pain often is of relatively long duration, for example, months or years and can be continuous or intermittent.

Antibodies of the present invention can be used to treat chronic pain or acute pain.

The treatment of chronic pain is preferred

The use of anti-TrkA antibodies in treating pain is discussed in WO 00/73344, in WO 05/061540 and in WO 06/131952 for example.

The pain may for example be associated with any of the following: pancreatitis, kidney stones, endometriosis, IBD, Crohn's disease, post surgical adhesions, gall bladder stones, headaches, dysmenorrhea, musculoskeletal pain, sprains, visceral pain, ovarian cysts, prostatitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondilitis, periarticular pathologies, oncological pain, pain from bone metastases, HIV infection.

Various models are known for assessing pain and can be used in screening antibodies/derivatives thereof.

For example, the nociception hot plate test can be used, as disclosed in WO 00/73344, for example. The experiment can be carried out according to McMahon et al., Nature Medicine, 1, 774-780 (1995), using the antibody/derivative as immunoadhesin. The antibody/derivative is infused subcutaneously into hind paw of an adult rat for a period of three weeks or by an osmotic mini-pump. The nociception sensitivity is evaluated at intervals using a hot plate test (Eddy and Leimbach, J. Phar. Exp. Ther., 107, 385-393 (1953)), which mimics hyperalgesia situations following inflammation or partial damage to the nerve. The nociceptive stimulus induces in such a case a response (paw licking and/or jumping) which presumes an integrated coordination higher than simple reflex. According to the test the animal is put in a pen having a plate heated to the desired temperature as base, usually 56° C. The latency of any of two responses (paw licking and jumping) is measured in control animals (treated with non relevant antibody) and in those treated with the anti-TrkA antibody/derivative.

As an alternative to the hot plate test, the nociceptive response to formalin can be assessed.

This test is disclosed by Porro and Cavazzuti in Prog. Neurobiol., 41:565-607 (1993) and was used in WO 06/137106. It involves assessing the reduction in pain response by analyzing any subsequent reduction in paw licking when a given candidate is administered prior to testing. Saline is typically used as a negative control.

The Chronic Constriction Injury (CCI) model is also a well known animal model. It involves chronic constriction of the sciatic nerve and is used for assessment of chronic pain of a neuropathic nature. This model is described by Bennett and Xie in Pain, 33, 87-107 (1988). It was used in WO 06/131592, for example.

Cancer

The antibodies/derivatives can also be used in the treatment of cancer.

Various cancers express TrkA. The interaction of TrkA with NGF may be involved in tumour development (e.g. of prostate and pancreatic cancers). Indeed in certain forms of cancer, an excess of NGF can facilitate the growth and infiltration of nerve fibres. By blocking the action of NGF it is possible to significantly reduce the formation of neuromas.

Furthermore, as an alternative to simply providing a blocking effect, the antibodies/derivatives can be coupled to a cytotoxic agent and can be used to target cancer cells expressing TrkA, as discussed later in further detail.

It is not however necessary to couple the antibodies/derivatives to toxins. ADCC (antibody-dependent cell-mediated cytotoxicity) arises due to an immune response in which antibodies/derivatives, by coating target cells, can make them vulnerable to attack by the system (e.g. by T cells, by complement activation, etc.)

Neuronal Disorders

The antibodies/derivatives can also be used in the treatment of various neuronal disorders.

As indicated above the antibodies/derivatives can be used to reduce the formation of neuromas.

They can also be used in the treatment of neurodegenerative disorders. As discussed earlier, NGF has potential use in the treatment of Alzheimer's disease, but has undesired agonist properties, including an increase in pain sensitivity. Antibodies/derivatives of the present invention may be useful in such treatments to reduce undesired agonist effects of NGF (see also the "Combination therapy" section below).

Furthermore, the antibodies/derivatives can be used to treat neuropathic pain, as discussed above. This may be associated with a lesion or a dysfunction of the nervous system.

Inflammatory Disorders

A still further application is in the treatment of inflammatory disorders.

NGF is released by mast cells, fibroblasts and other cell types in the peripheral sites where inflammatory processes occur. In particular, mast cells appear to play a fundamental role. They produce NGF and at the same time express functional TrkA receptors at their surface. The NGF/TrkA system appears to mediate mastocyte activation through an autocrine positive feedback mechanism which allows local amplification of the algogenic inflammatory signal. Examples of inflammatory disorders that may be treated include inflammatory forms of the urinary tract and of the pelvic region, osteoarthritis, rheumatoid arthritis, asthma.

Other Disorders

As discussed earlier, NGF has potential use in the treatment of diabetes and leprosy, but has undesired agonist properties, including an increase in pain sensitivity. Antibodies/derivatives of the present invention may be useful in such treatments to reduce undesired agonist effects of NGF (see also the "Combination therapy" section below).

Combination Therapy

Antibodies or derivatives thereof of the present invention may be used together with one or more other active agents in combination therapy. They may be used for simultaneous, sequential or concerted administration in medicine.

For example, the antibody or derivative may be combined with an analgesic opioid. WO 06/137106 explains that small amounts of molecules able to block TrkA biological activity can potentiate the analgesic effects of opioids.

Such opioids include one or more compounds selected from the following: morphine, codeine, dihydrocodeine diacetylmorphine, hydrocodone, hydromorphone, levorphanol, oxymorphone, alfentanil, buprenorphine, butorphanol, fentanyl, sufentanyl, meperidine, methadone, nabulfina, propoxyphene, pentazocine, and their pharmaceutically acceptable derivatives thereof (e.g. pharmaceutically acceptable salts thereof).

Alternatively, the antibody or derivative may be used in combination therapy with one or more non-opioid analgesic.

A further combination is that of the antibody or derivative with NGF. As discussed above, the use of NGF in the treatment of various disorders, including Alzheimer's disease, diabetes mellitus, leprosy, etc., had been proposed, but increases in pain sensitivity had been noted arising from agonist properties towards peripheral targets. Again, by using an antibody or derivative of the present invention, pain sensitivity can be reduced, thereby making NGF-based therapies more attractive.

A further combination is that of one or more antibodies or derivatives of the present invention together with one or more other antibodies. A preferred combination is with one or more other anti-TrkA or anti-NGF antibodies. Such combinations may provide increased efficacy in treating one or more of the disorders discussed herein, relative to treatment with a single antibody. For example combinations of two or more antibodies found to be amongst the most effective in assay procedures used herein may be used.

Pharmaceutical Compositions, Vehicles and Routes of Administration

The antibodies/derivatives of the present invention can be administered by any appropriate route.

This includes (but is not limited to) intraperitoneal, intramuscular, intravenous, subcutaneous, intratracheal, oral, enteral, parenteral, intranasal or dermal administration.

Thus the invention provides a pharmaceutical composition comprising an antibody or derivative thereof together with a pharmaceutically acceptable carrier or excipient.

The antibodies/derivatives can typically be administered for local application by injection (intraperitoneal or intracranial-typically in a cerebral ventricle-or intrapericardiac or intrabursal) of liquid formulations or by ingestion of solid formulations (in the form of pills, tablets, capsules) or of liquid formulations (in the form of emulsions and solutions).

Compositions for parenteral administration commonly comprise a solution of immunoglobulin dissolved in a compatible, preferably aqueous solution. The concentration of the antibody/derivative in these formulations can vary from less than 0.005% to 15-20% w/v. It is selected mainly according to the volumes of the liquid, viscosity, etc, and according to the particular administration mode desired.

Alternatively, the antibodies/derivatives can be prepared for administration in solid form. The antibodies can be combined with different inert or excipient substances, which can include ligands such as microcrystalline cellulose, gelatin or Arabic rubber; recipients such as lactose or starch; agents such as alginic acid, Primogel or corn starch; lubricants such as magnesium stearate, colloidal silicon dioxide; sweeteners such as saccharose or saccharin; or flavours, such as mint and methyl salicylate. Other pharmaceutical administration systems include hydrogel, hydroxymethylcellulose, liposomes, microcapsules, microemulsions, microspheres, etc Local injections directly at a site affected by a disorder/close thereto is a preferred mode of administration if a disorder is localised.

In contrast to anti-tumour based therapies, WO 06/131952 discusses the use of various anti-TrkA antibodies in the treatment of pain.

Here it is explained that anti-TrkA antibodies are suitably administered systemically. Systemic administration can be performed by injection, e.g. continuous intravenous infusion, bolus intravenous infusion, subcutaneous or intramuscular injection. Alternatively, other forms of administration (e.g. oral, mucosal, via inhalation, sublingually, etc.) may also be used.

If desired, however, delivery of the antibody/derivative can be performed by local administration (e.g. intra-articular injection or subcutaneous, intramuscular injection) in the vicinity of affected tissues.

The anti-TrkA antibody/derivative will suitably be formulated in a pharmaceutical composition appropriate for the intended route of administration. Solutions for injection will suitably contain the antibody/derivative dissolved or dispersed in an aqueous medium (e.g. water for injection) as appropriate containing appropriate buffers and molarity modifiers (e.g. phosphate, salt and/or dextrose).

The treatment regime (i.e. dose, timing and repetition), can be represented by single or repeated administrations (e.g. injections) of the product by the chosen administration route.

The interval of dose administration can be subject to modifications depending on the extent and duration of the clinical response, as well as the particular individual and the individual clinical history.

Suitably the anti-TrkA antibody/derivative has a long duration of action. In particular the clinical effect of the antibody following administration may be as long as 21 days as determined from animal studies. Furthermore, anti-TrkA antibodies/derivatives may manifest clinical benefit for a longer period than that in which its presence can be detected in a relevant biological matrix such as serum or plasma following its administration.

In light of the intended long duration of action (i.e. an effect suitably lasting at least one week, or preferably at least two weeks e.g. at least three weeks or at least four weeks), suitably the antibody/derivative may be administered to subjects at a frequency of not more than once per week e.g. not more than once per two weeks or once per three weeks or once per four weeks.

A suitable daily dose of the anti-TrkA antibody/derivative will typically range from 0.1 mg/kg to 10 mg/kg body weight.

(Using humanised anti-TrkA antibodies and a CCI model it is reported in WO 06/131592 that significant analgesic properties were observed in experimental animals at a dosage of 2 mg/kg, although lower dosages may of course be preferred for humans.)

Turning now to administration in respect of tumours, administration may be through direct and localized injection into a tumour or a tissue near the tumour site. For systemic administration, doses vary from 0.05 mg/kg per day to 500 mg/kg per day, although dosages in the lower region of the range are preferred because they are easier to administer. Dosages can be calibrated for example to guarantee a particular level in the plasma of the antibody/derivative (in the range of about 5-30 mg/ml, preferably between 10-15 mg/ml) and maintain this level for a given period of time until the clinical results are achieved.

Effective methods for measuring or assessing the stage of pancreatic or prostatic tumours are based on the measurement of the prostate specific antigen (PSA) in blood, on the measurement of the survival time for pancreas tumours, on the measurement of the slowing or inhibition of diffusion for metastases in the case of both tumour types.

For direct injection at the level of a tumour site, dosage depends on different factors including the type, stage and volume of the tumour, along with many other variables.

Depending on tumour volume, typical therapeutic doses may vary from 0.01 mg/ml to 10 mg/ml injections which can be administered with the necessary frequency.

Whatever the nature of the therapy, humanised antibodies/derivatives may be eliminated much more slowly and require lower dosages to maintain an effective level in the plasma than non-humanised antibodies. Moreover, with high affinity antibodies/derivatives, administration may be less frequent and less sizable than with antibodies having lower affinity.

The therapeutically effective dosage of each antibody/derivative can be determined during the treatment by a skilled medical practitioner. If necessary, dosages can be reduced (e.g. to reduce side effects) or increased (to increase activity).

Prior to administration, preparations of antibodies/derivatives of the invention can be stored by being frozen or lyophilized. They may then be reconstituted immediately before use in a suitable buffer. Given that lyophilisation and reconstitution can result in a loss in activity, antibody administration levels can be calibrated to compensate for this fact (For conventional immunoglobulins, IgM antibodies tend to have a greater loss of activity than IgG antibodies.) A shelf life may also be assigned so that antibodies/derivatives are not used after a certain period of storage.

Diagnostic and Prognostic Applications

An antibody or derivative thereof of the present invention can be used in the diagnosis or prognosis of any of the diseases/conditions discussed above in relation to medical uses.

For example it may be used to facilitate detection of TrkA positive tumour markers, as a precocious marker of the insurgence of Alzheimer's disease, etc.

It may also be used in the diagnosis of CIPA ("congenital insensitivity to pain with anhydrosis"). This is a hereditary, recessive, autosomal syndrome characterised by recurrent episodic fever, anhydrosis, the absence of reaction to nociceptive stimuli, mental retardation and a tendency to self-mutilation. It results from mutations in the TrkA gene. Indeed an antibody or derivative of the present invention may be used in the diagnosis or prognosis of a wide range of conditions involving aberrant expression of TrkA (compared to expression of TrkA in a healthy individual or a healthy tissue sample).

The present invention therefore includes within its scope a method comprising obtaining a biological sample obtained from a patient and contacting the sample with an antibody or derivative of the present invention.

If desired, the antibody/derivative may be immobilised. It may be provided in the form of a diagnostic kit.

The method may then include assaying the binding of the antibody/derivative to said sample in a quantitative or qualitative manner. If desired, this may be done with reference and/or to a positive control (indicating a healthy state) or a negative control (indicating the presence/likelihood of a disorder).

For diagnostic purposes, the antibodies/derivatives can be both marked with a detectable marker or can be unmarked. (The term "marker" is used herein to include labels or any other detectable moiety/moiety that can trigger a detectable change.)

Unmarked antibodies can be used in combination with other marked antibodies (secondary antibodies), which are reactive against humanised, or human antibodies (e.g. specific antibodies for the constant regions of human immunoglobulins).

Alternatively, antibodies can be marked directly. A wide variety of markers can be used, e.g. radionuclides, fluorophores, colourings, enzymes, enzymatic substrates, enzymatic factors, enzymatic inhibitors, ligands, etc.

In particular, for diagnostic or prognostic imaging applications, a detectable agent is conjugated to the antibody that is detectable or marked with a detectable radioisotope (e.g. a radioisotope such as of iodine, indium, technetium) or in paramagnetic manner (with paramagnetic atoms or ions, such as transition elements, actinides and rare earths, in particular, manganese II, copper II and cobalt II).

Imaging procedures may entail the intravenous, intraperitoneal or subcutaneous injection (in lymphatic drainage regions to identify lymph node metastases) and may use detectors of radionuclide emissions (such as scintillation β counters) in the case of immunoscintigraphy.

If a paramagnetic marking is used instead, an NMR spectrometer can be used.

Other Applications

The antibodies/derivatives thereof may be used as starting points to develop further antibodies. Thus they may be used as design tools.

They may be screened by one or more binding/functional assays and may therefore be part of a drug development program.

They may be used for tissue typing, for forensic studies, etc.

They may be used as research tools

For example they may be used for further research into TrkA and/or into disorders in which TrkA binding to NGF (or other TrkA binding agents) may be implicated. They may be used to study binding and/or activation All of the above applications of the antibodies/derivatives are within the scope of the present invention.

Nature of Antibodies and Antibody Derivatives

It will be appreciated from the foregoing description that a wide range of antibodies and derivatives thereof can be used in the present invention.

For the avoidance of doubt the terms "antibodies" and "antibody derivatives" are discussed below in further detail.

Antibodies

Antibodies of the present invention can be in the form of any desired immunoglobulin structure.

IgG and IgM are however preferred, with IgG being the most preferred. Of the IgG isoforms, IgG1 is preferred, but other forms can be used including IgG4.

The antibodies are chimeric, i.e. they include one or more regions that are normally not associated with one another in nature. More specifically, one or more murine-derived CDR regions are present in the antibodies, but other regions (especially constant regions) are preferably human or humanised.

Humanised regions have more residues in common with a given human immunoglobulin region than with a corresponding mouse immunoglobulin region. Preferably, they have at least 75%, at least 80%, at least 85%, at least 90%, at least 95% or at least 98% identical with the human region at the amino acid sequence level. More preferably, there is 100% sequence identity over one or more non-CDR regions (e.g. constant regions).

In some cases, however it may be beneficial to introduce certain changes.

For example, it may be desirable to introduce changes that prevent/reduce one or more of the following:
a) activation of the complement system
b) complement mediated lysis
c) activation of T cells
d) binding to an Fc receptor.

Mutations indicated to allow one more of the above to be achieved are discussed in various patents. One or more of said mutations may therefore be included in antibodies/derivatives of the present invention For example, U.S. Pat. No. 6,194,551 proposes amino acid substitutions at amino acid positions 322, 329 and/or 331 (using the Kabat numbering system) of the constant heavy chain region of the IgG molecule and suggests that they can be used to prevent/reduce undesired activation of the complement system by abolishing Fc binding to C1q (see also Ward and Ghetie, Therapeutic Immunology 2: 77-94 (1995)). U.S. Pat. No. 6,194,551 explains that proline is conserved at position 329 in human IgG's. This residue (which is glycosylated and may thereby be involved in activating the complement system) is preferably replaced with alanine. However, substitution with any other amino acid is contemplated, e.g., serine, threonine, asparagine, glycine or valine. U.S. Pat. No. 6,194,551 explains that proline is also conserved at position 331 in human IgG1, IgG2 and IgG3, but not IgG4 (which has a serine residue at position 331). Residue 331 is preferably replaced by alanine or another amino acid, e.g. serine (for IgG regions other than IgG4), glycine or valine. A further possibility discussed is to introduce substitutions at position 322. Lysine 322 is conserved in human IgGs, and this residue is said to be preferably replaced by an alanine residue, although a substitution with any other amino acid residue is contemplated (e.g. serine, threonine, glycine or valine).

U.S. Pat. No. 6,491,916 discloses that mutations in the region spanning about position 230 to about position 240 of a humanised antibody can produce particular advantages. Here it is explained that comparisons of antibodies that bind to Fc to those that do not bind to Fc suggest that changes in this region result in anti-CD3 antibodies that do not activate T cells. For example, some of the preferred antibodies comprise a mutation at position 234, at position 235, or at both. Anti-CD3 antibodies comprising one, two, three, four, five, or more mutations at one or more of positions 230, 231, 232, 233, 234, 235, 236, 237, 238, 239, or 240, are expected to have advantages. This patent also discloses that an antibody having an IgG1 Fc region and mutated to have alanine at both positions 234 and 235 does not bind to the C1q component of complement and start the complement-mediated cascade. Further, it is explained that the mutation Lys 320 to Gln has an affinity for C1q only slightly weaker than the wild type but is non lytic.

U.S. Pat. No. 5,624,821 discloses that by changing any one of residues 318 (Glu), 320 (Lys) and 322 (Lys), to Ala, it is possible to abolish C1q binding. It points out that it is not necessary to replace the ionic residues only with Ala to abolish C1q binding, but that it will also be possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. It will also be possible to use such polar non-ionic residues as Ser, Thr, Cys, and Met in place of residues 320 and 322, but not 318, in order to abolish C1q binding activity. U.S. Pat. No. 5,624,821 further discloses that replacing residue 297 (Asn) with Ala results in removal of lytic activity while only slightly reducing (about three fold weaker) affinity for C1q. It explains that it is thought this arises because the alteration destroys the glycosylation site and that the presence of carbohydrate is required for complement activition. It points out that any other substitution at this site will also destroy the glycosylation site. U.S. Pat. No. 5,624,821 also discloses that mutations on, adjacent or close sites in the hinge link region (e.g. replacing residues 234, 236 or 237 by Ala) indicate that alterations in residues 234, 235, 236 and 237 at least affect affinity for the Fc gamma R1 receptor.

Of course one or more amino acid changes (typically conservative amino acid changes) may be incorporated that do not substantially affect biological properties. Possible mutations are therefore not restricted to those discussed above.

Antibodies of whatever nature can be provided in monoclonal form (i.e. in combination with identical antibodies) or polyclonal form (i.e. in combination with different antibodies). Hybridomas capable of producing monoclonal antibodies of the present invention are also within the scope of the present invention.

Antibody Derivatives

The term "antibody derivatives" is intended to allow for a wide range of structural changes that can be made relative to an antibody, provided that desired functional properties are retained.

Thus, for example, binding affinity to TrkA is desirably retained.

Preferably, the derivatives are also effective in one or more of the functional assays described herein.

For the avoidance of doubt it is noted that all of the following are considered to be derivatives of an antibody of the present invention:

a) a fragment of said antibody b) a multimer comprising a plurality of fragments of said antibody (referred to herein as a "fragment multimer")

c) a fusion product of said antibody, fragment or fragment multimer and another moiety d) a variant of said antibody, fragment, fragment multimer, or fusion product, having at least 75% sequence identity therewith.

Thus the term "derivative" is interpreted broadly.

Turning now to fragments of the present invention, these are preferably at least seven amino acids long (Thus they are at least as long as the shortest CDR region shown in FIGS. 1a & 1b for the heavy and light chains of the present invention). More preferably, they are at least ten, at least fifteen, or at least twenty amino acids long.

They can be produced, by means of proteolytic digestion starting from intact antibodies or by inserting stop codons in the desired positions in vectors bearing the coding DNA sequences for the variable regions of the heavy and light chain. This can be done after the $CH_1$ region to produce Fab fragments or after the hinge region to produce $(Fab')_2$ fragments.

Derivatives in the form of ScFv chains can be obtained by joining the variable regions of the heavy chain and of the light chain by means of a linker (Huston et al, PNAS, 85, 5879 (1988); Bird et al, Science, 242,423 (1988)). Fv or Fab fragments can be expressed in *E. coli* (Buchner and Rudolph, Bio/Technology, 9, 157 (1991); Skerra et al., Bio/Technology, 9, 273 (1991)) or also in eukaryotic cells, preferably mammal derived.

Indeed a very range of fragment forms is possible, including those discussed by Holliger & Hudson in Nature Biotechnology, Vol 23, No 9, 1126-1136 (2005).

They can include fragments consisting of individual VH or VL chains (sometimes known as "domain antibodies" or "dAbs") or even fragments of said chains (e.g. individual CDR regions). These are all within the scope of the present invention. Multimeric forms are also included, such as minibodies, bis(or higher)-ScFv, diabodies, triabodies, tetrabodies, Fab multimers, etc. (referred to herein as "fragment multimers").

Furthermore, various other moieties can be covalently linked with antibodies/fragments of the present invention so as to provide beneficial properties. Such "fusion products" are within the scope of derivatives of the present invention. The moiety may for example be a diagnostic agent, a therapeutic agent, a marking agent, an agent that increases the half life of the product, or an agent that reduces immunogenicity (preferably in a human host).

For example, fusion products in the form of PEGylated antibodies/fragments may be provided. PEG has been predominantly used to reduce the immunogenicity and increase the circulating half-lives of antibodies. It may also have a beneficial effect on the use of antibodies in certain clinical settings such as tumour targeting.

The parts of a fusion product can be linked together chemically. For example this may be done by cross-binding using heterobifunctional agents (e.g. SPDP, carbodiimide, glutaraldehyde, etc.).

In the case of fusion proteins, these are preferably made using genetic engineering techniques. Thus appropriate coding sequences based on the genetic code can be provided encoding the desired fusion protein and can then be cloned into a host cell using a suitable expression vector. Expression may be under the control of a constitutive or inducible promoter. The expressed fusion protein can be purified using standard techniques (e.g. by using immunoffinity procedures). Cell-based or cell-free expression systems may be used.

Fusion proteins may for example comprise antibodies/fragments of the present invention fused to cytotoxins. Resultant fusion proteins may then be used to target cells that express TrkA receptors, e.g. TrkA expressing tumour cells.

The production of various cytotoxic immunotoxins is reported by Thorpe et al, Monoclonal Antibodies in Clinical Medicine, Academic Press, 168 (1982). Indeed a large number of cytotoxic agents are suitable for use in immunotoxins. Such agents include radionuclides such as iodine 131 or other isotopes of iodine, yttrium 90, rhenium 188 and bismuth 212 or other isotopes that emit alpha particles, a great number of chemotherapeutic drugs such as vindesin, methotrexate, adriamycin and cisplatin; cytotoxic proteins, such as proteins that inhibit ribosomes (e.g. pokeweed antiviral protein, *Pseudomonas* exotoxin A, diphtheria toxin, ricin A and clavin of vegetable origin), or agents active at the cell surface level (e.g. phospholipase enzymes such as Phospholipase C).

Sometimes the cytotoxic region of the immunotoxin can be immunogenic and consequently limit the clinical usefulness of the fusion protein in case of chronic or long term therapy.

An alternative to avoid the problem of the immunogenicity is to express in fusion with the binding domain of the antibody/derivative a protein able to interact with DNA and bind to this fusion protein the vector (e.g. plasmid) that contains the toxin expression cassette. The numerous positive charges of protamin, a human protein that binds DNA, can interact in stable fashion with the negative charges of the DNA, generating a fusion partner for the neutral charge antibody/derivative. This is much more stable and less immunogenic than the toxin itself. After internalization of the antibody-vector complex via receptor mediated endocytosis, the expression of the toxin causes the death of the cell.

Moreover, if desired, inducible or cell-specific promoters can be provided in the toxin expression cassette. This approach is aimed at maximizing the selective elimination of tumour cells while minimizing toxicity side effects (Chen et al, Gene Ther., 2, 116 (1995)).

Fusion proteins may also include fusions with other antibodies/derivatives. For example fusions of dAbs to specific antigens with other dAbs capable of binding long lasting serum proteins (e.g. serum albumin) have been used to increase serum half life.

Variable heavy and light chain sequences of the present invention may form part of multivalent antibodies having specificity for one or more antigens, one of which is TrkA, or one or more epitopes within TrkA.

Multivalent antibodies with specificity for one or more antigens, one of which is TrkA Expression Systems Many expression systems can be used to provide antibodies/derivatives of the present invention.

For example, prokaryotic systems can be used and are well characterized.

*E. coli* is one of the prokaryotic hosts that is particularly useful for cloning the DNA sequences of the present invention. Moreover, a great number of well characterized promoters is available, e.g. from the lac or trp operon or β-lactamase or λ phage. Typically, these promoters control expression and bear binding site for the ribosome, for the correct start and finish of transcription and translation. It is possible to increase the half-life of the humanised immunoglobulins of the invention produced in prokaryotic systems by conjugation with polyethylene glycol (PEG).

Other single-cell organisms, such as yeasts, can be used for expression. The host of choice is *Saccharomyces*, using suitable carriers provided with expression control, replication termination and origin sequences.

Phage-display libraries bearing sequences of the variable regions of immunoglobulins have been well reported and can be used in binding studies [Cesareni, FEBS Letts, 307, 66 (1992); Swimmer et al. PNAS, 89, 3756 (1992); Gram et al. PNAS, 89, 3576 (1992); Clackson et al. Nature, 352, 624 (1991); Scott & Smith, Science, 249, 386 (1990); Garrard et al. Bio/Techniques, 9,1373 (1991)].

Insect cell cultures can also be used, typically utilising cells of S2 *Drosophila* transfected in stable fashion or cells of *Spodoptera frugiperda* with the expression system based on the Baculovirus (Putlitz et al. Bio/Technology, 8, 651 (1990)).

Plants and cultures of vegetable cells can even be used (Larrick & Fry, Hum. Antibodies Hybridomas, 2, 172 (1991); Benvenuto et al. Plant Mol. Biol, 17 865 (1991); Durin et al. Plant Mol. Biol; 15,281 (1990); Hiatt et al. Nature, 342,76 (1989))

It is also possible to use tissue cultures of mammal cells to express the polypeptides of the present invention. This can be advantageous in obtaining human glycosylation patterns. Different isotypes can be expressed. IgG1 has proven to be the most effective isotype in the induction of the immune response (Winnacker, From Genes to Clones, VCH Publishers, NY, (1987)) whilst IgG4 is often used for diagnostic applications (Riechmann et al., Nature, 332,323 (1988)).

Mutated forms abolishing/reducing activation of complement may also be provided, as discussed earlier with reference to U.S. Pat. Nos. 6,194,551, 5,624,821 and/or 6,491, 916.

In particular, mammalian cells are preferred. A great number of host cell lines have been developed for the secretion of intact immunoglobulins, among them are CHO cell lines, several COS cell lines, the HeLa cells, myeloma cell lines (NSO, SP/2, YB/0 e P3×63.Ag8.653), transformed B cells or hybridomas. Expression vectors for these cells can include expression control sequences, such as a replication origin, a promoter, an enhancer (Queen et al, PNAS, 86:10029 (1989)), and the sequences required for ribosome binding, RNA splicing and polyadenylation, and sequences for transcription termination. The expression control sequences of choice are promoters derived from immunoglobulin genes and from viruses, such as SV40, Adenovirus, Bovine Papilloma Virus, Cytomegalovirus and the like. Generally, the expression vector includes a selectable marker, such as the resistance to neomycin.

For the expression of humanised antibodies, it is preferable to cultivate the mammal cell lines with a serum-free medium. For example, the HUDREG-55 cell line can easily be grown in Serum-Free and Protein-Free Hybridoma Medium Cat. No. S-2897 from Sigma (St. Louis, Mo.).

Nucleic Acids, Vectors, Transgenic Animals

Nucleic acid sequences encoding the antibodies/derivatives/antibody chains of the present invention can be produced by standard techniques, given that the amino acid sequences for the key variable regions are provided herein and that corresponding coding sequences can be provided using the genetic code. These sequences can be incorporated into expression vectors and/or cloned into cells.

Indeed techniques for producing and cloning "reshaped antibodies" with rodent CDR regions and humanised framework regions are now well known. They are discussed for example in Jones, Dear, Foote, Neuberger and Winter, Nature, 321, 522-4 (1986); in Riechmann, Clark, Waldman and Winter, Nature, 332, 323-327 (1988) and in Verhoeyen, Milstein and Winter, Science, 239, 1534-1536 (1988).

Such nucleic acids can be incorporated into expression vectors, including plasmids, phage, etc., as is well known in the art and is discussed above.

Nucleic acids of the present invention can also be used to design probes or primers. These can be used for example to isolate or amplify nucleic acids of the present invention.

Probes or primers are therefore within the scope of the present invention. Typically they are at least 10, at least 15 or at least 20 bases long. Preferably they hybridise under stringent conditions to nucleic acid strands that encode antibodies/derivatives of the present invention or to complementary strands thereof. One example of stringent hybridisation conditions involves using a pre-washing solution of 5×SSC, 0.5% SDS, 1.0 mM EDTA (pH 8.0) and attempting hybridisation overnight at 55° C. using 5×SSC. However, there are many other possibilities. Some of these are listed in Table 1 of WO98/45435, for example (See especially the conditions set out under A-F of that table and, less preferably, those listed under G to L or M to R.).

In a further aspect of the present invention, the nucleic acids can advantageously be used to provide transgenes for use in producing non-human transgenic animals, preferably mice. Here the antibody/derivative may be expressed in an inducible way, or under the control of constitutive promoters.

Such animals can be advantageously used to study and test drugs for human pathologies wherein the NGF/TrkA interaction is inhibited and, particularly, neurodegenerative pathologies.

The antibody/derivative can be advantageously expressed in a retrievable body fluid such as milk or serum, from which it can be retrieved and purified using standard techniques.

Transgenes used to produce the transgenic animals may comprise the relevant coding sequence(s) operatively bound to a promoter, usually in combination with an enhancer sequence, such as that of the rodent immunoglobulin or the promoter/enhancer of the casein gene (Buhler et al., Bio/Technology; 8,140 (1990); Meade et al., Bio/Technology, 8, 443 (1990)).

The transgenes can be transferred into the cells or embryos by means of homologous recombination. A wide range of non-human transgenic animals can be produced, including mice, rats, sheep, cows, goats, etc. (see WO 91/08216).

It will be appreciated from the foregoing description that the present invention provides a range of new antibodies, derivatives, nucleic acids, etc.

If desired, these can be provided in substantially purified form. For the purposes of the present invention this means that they are the majority of the dry weight of a particular composition. For example they may represent at least 60%, at least 70%, at least 80%, at least 90%, at least 95%, or at least 98% of said dry weight.

They may be provided in isolated form. This means that they are removed from one or more other components with which they may be normally associated in nature (For example a nucleic acid may be provided in a form that is isolated from a cell).

They may be provided in a variety of other forms. For example they may be fused to heterologous moieties and/or they may be immobilised.

All of the above forms are within the scope of the present invention.

BRIEF DESCRIPTION OF THE DRAWINGS

The present invention will now be described by way of example only, with reference to the accompanying drawings, wherein:

FIGS. 1a & 1b show amino acid sequence alignments for various heavy and light chains.

FIG. 2 shows the results for antigen binding specificity towards TrkA-IgG in respect of supernatants from various clones resulting from an experiment involving transient expression of the humanised MNAC13 variants in COS-7 cells.

FIG. 3 the results of an experiment in which cellular binding of the antibodies to TrkA expressed on TF-1 cells was analysed by cytofluorimetric analysis.

FIG. 4 shows the results of a further analysis in which the best binders identified from FIG. 3 (BXhVH3VL3, BXhVH5VL1, BXhVH5VL3, and HuMNACWOv) were compared to HuMNACWO.

FIG. 5 shows the results of an assay in which different humanised candidates were assayed in parallel with murine MNAC13 antibody (muMNACEP), chimMNAC13, HuMNACWO, and Human IgG1 as standard control.

FIG. 6 shows the heavy and light chains for BXhVH5VL1, including the constant regions (the first amino acid of the constant region is underlined.)

FIG. 7 shows the heavy chain for BXhVH5VL1 N297A, including the constant region (the first amino acid of the constant region is underlined and the 297A position is bold and underlined).

FIG. 11 shows an experiment demonstrating the analgesic effect of local intradermic injection of BXhVH5VL1 N297A or control hIgG when co-injected with rhNGF FIG. 12 shows an experiment demonstrating the analgesic effect of local intradermic injection of muMNACEP or control mIgG when co-injected with rhNGF

EXAMPLES

Figure 8:
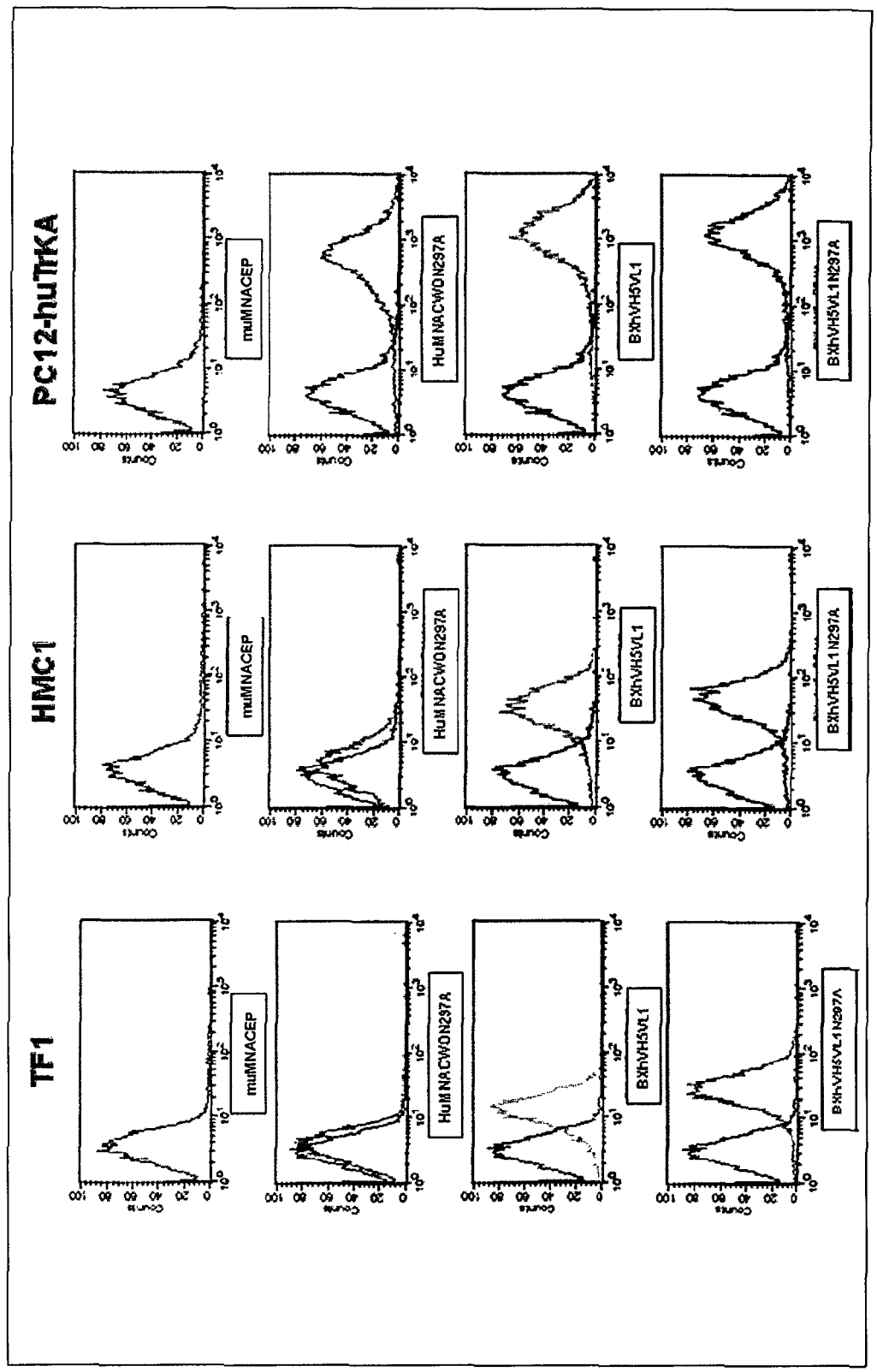
FIG. 8 shows BXhVH5VL1 and BXhVH5VL1 N297A binding to cell lines expressing huTrkA.

Before discussing the examples in detail, some of the nomenclature used therein is set out below:

muMNACEP

This term is used to indicate the murine antibody MNAC13, as disclosed in EP1181318 The heavy chain variable region of this antibody is referred to herein as mVHEP (SEQ ID NO. 15). The light chain variable region is referred to herein as mVLEP (SEQ ID NO. 16).

HuMNACWO

This term is used to indicate the humanised antibody MNAC13 disclosed in WO 05/061540

The heavy chain variable region of this antibody is referred to herein as HuVHWO (SEQ ID NO. 17). The light chain variable region is referred to herein as HuVLWO (SEQ ID NO. 18)

HuMNACWOv

This terms is used to indicate a variant of the antibody disclosed in HuMNACWO (see above) in which the heavy chain CDR3 region has been replaced with a CDR3 region corresponding to that present in muMNACEP. The variant is novel and is within the scope of the present invention.

The heavy chain variable region of this antibody is referred to herein as HuVHWOv (SEQ ID NO. 6). The light chain variable region can be referred to herein as HuVL-WOv. However, in order to avoid duplication, it is not shown in FIG. 1b, because it is the same as HuVLWO (SEQ ID NO. 18).

ChimMNAC13

This corresponds to muMNACEP, but has human constant regions instead of mouse constant regions.

The heavy chain variable region of this antibody is referred to herein as mVHEP (SEQ ID NO. 15)

The light chain is referred to herein as mVLEP (SEQ ID NO. 16)

```
3-23*01,        (SEQ ID NO. 19)

JH4,            (SEQ ID NO. 20)

L6*01           (SEQ ID NO. 21)
and

JK1             (SEQ ID NO. 22)
```

These are coding sequences derived from human germline genes.

They are used for assessing degrees of humanisation in Table 1. Thus if there are no changes relative to a human germline sequence it is considered that there is 100% humanisation.

$$\text{The percentage humanisation} = \frac{\text{number of changes}}{\text{total number of residues compared}} \times 100$$

The table below shows the percentage humanisation for the different variants:

TABLE 1

| Sequence variant | Number of murine AA in the FW/number of total AA in the FW | % Humanisation (related to FW sequence) | Number of murine AA including CDR AA/number of total AA in the variable region | % humanisation (related to complete variable sequence) |
| --- | --- | --- | --- | --- |
| BXhVH1 | 0/87 | 100 | 36/123 | 70.7 |
| BXhVH2 | 3/87 | 96.6 | 39/123 | 68.3 |
| BXhVH3 | 3/87 | 96.6 | 39/123 | 68.3 |
| BXhVH4 | 3/87 | 96.6 | 39/123 | 68.3 |
| BXhVH5 | 5/87 | 94.2 | 41/123 | 66.7 |
| BXhVHWO | 12/87 | 86.2 | 48/123 | 61.0 |
| BXhVL1 | 0/80 | 100 | 26/106 | 75.5 |
| BXhVL2 | 4/80 | 95 | 30/106 | 71.7 |
| BXhVL3 | 6/80 | 92.5 | 32/106 | 69.8 |
| BXhVL4 | 6/80 | 92.5 | 32/106 | 69.8 |
| BXhVL5 | 6/80 | 92.5 | 32/106 | 69.8 |
| BXhVL6 | 8/80 | 90 | 34/106 | 67.9 |
| BXhVL7 | 8/80 | 90 | 34/106 | 67.9 |
| BXhVL8 | 11/80 | 86.2 | 37/106 | 65.1 |
| BXhVLWO | 9/80 | 88.8 | 35/106 | 67 |

It can be seen that all of the variant variable chains have a degree of humanisation over the framework regions of over 85%.

"BX" Sequences

The sequences labelled with a code beginning with "BX" are novel sequences of the present invention. The letters following "BX" are either VH or VL to indicate a heavy or light variable chain respectively. The sequences are then simply numbered consecutively in the order in which they are shown in FIGS. 1a & 1b for a given chain.

There are five heavy chain sequences. Thus they are numbered:

```
BXhVH1          (SEQ ID NO. 1)
BXhVH2          (SEQ ID NO. 2)
BXhVH3          (SEQ ID NO. 3)
BXhVH4          (SEQ ID NO. 4)
BXhVH5          (SEQ ID NO. 5)
```

There are eight light chain sequences. Thus they are numbered:

```
BXhVL1          (SEQ ID NO. 7)
BXhVL2          (SEQ ID NO. 8)
BXhVL3          (SEQ ID NO. 9)
BXhVL4          (SEQ ID NO. 10)
BXhVL5          (SEQ ID NO. 11)
BXhVL6          (SEQ ID NO. 12)
BXhVL7          (SEQ ID NO. 13)
BXhVL8          (SEQ ID NO. 14)
```

The chains can be combined in antibodies or derivatives thereof.

The forty possible combinations have all been produced and are:

```
BXhVH1VL1, BXhVH1VL2, BXhVH1VL3, BXhVH1VL4,
BXhVH1VL5, BXhVH1VL6, BXhVH1VL7, BXhVH1VL8,

BXhVH2VL1, BXhVH2VL2, BXhVH2VL3, BXhVH2VL4,
BXhVH2VL5, BXhVH2VL6, BXhVH2VL7, BXhVH2VL8,

BXhVH3VL1, BXhVH3VL2, BXhVH3VL3, BXhVH3VL4,
BXhVH3VL5, BXhVH3VL6, BXhVH3VL7, BXhVH3VL8,

BXhVH4VL1, BXhVH4VL2, BXhVH4VL3, BXhVH4VL4,
BXhVH4VL5, BXhVH4VL6, BXhVH4VL7, BXhVH4VL8,

BXhVH5VL1, BXhVH5VL2, BXhVH5VL3, BXhVH5VL4,
BXhVH5VL5, BXhVH5VL6, BXhVH5VL7, BXhVH5VL8.
```

"N297A"

The designation "N297A" after the name of an antibody indicated that position 297 of the heavy chain constant region is mutated from N to A.

The sequence of BXhVH5VL1 N297A is provided as SEQ ID No. 23.

Expression Vectors

The appropriate coding sequences were fused to a sequence coding for a secretory signal 5' and a splice donor sequence 3' to the cDNA for cloning into an antibody expression system. The DNA fragments were cloned into IgG1 expression vectors.

These expression vectors were based on genomic sequences encoding the human constant domains and cloning cassettes for the insertion of the selected cDNA fragments of the hVH and hVL sequences.

Transient Expression of the Humanised MNAC13 Variants in COS-7 Cells and Determination of Antibody Titers Each combination of Heavy and Light chain was transiently transfected in COS-7 cells and antibody titer was determined.

The expression vectors coding for the light chain and for the heavy chain were transiently cotransfected into COS-7 cells by lipofection using Lipofectamin according to the manufacturer's instructions (Invitrogen, Germany) in a 24-well format.

After transfection the medium was replaced by DMEM containing 10% FCS and 2%

L-glutamine and the supernatants of the COS-7 cells were collected 4 days after transfection.

The antibody titer of the humanised antibodies secreted into the supernatants of transfected COS-7 cells was analyzed by a sandwich ELISA.

Briefly, a mouse anti-human kappa chain recognizing antibody (BD) was immobilized on a 96 well plate, blocked and incubated with diluted supernatant of transfected COS-7 cells. The presence of antibodies was detected by a POD conjugated rabbit anti-human IgG (H+L) antibody (Dianova, Germany). A chimeric control antibody was used as a standard in concentrations from 1 to 10 ng/ml. The determined antibody concentrations were further adjusted by an internal standard sample having a standardized antibody concentration.

Example 1

Comparison of Humanised Antibody Binding Towards TrKA-IgG in ELISA

Based on the determined antibody concentration, supernatants of all samples were adjusted to the same antibody concentration.

The binding activities of all humanised antibody variants were analyzed by a TrkA-IgG antigen ELISA. They were compared to the binding activities of the ChimMNAC13 and HuMNACWOv.

Antibodies and antigens were thawed, aliquoted and stored at −20° C. Aliquots of the antibodies in use were stored at 4° C. for a maximum of two weeks.

Antigen ELISA was performed as follows: Maxisorb plates (Nunc, Germany) were coated with 0.125, 0.25, 0.5, and 1 μg/ml TrkA-IgG. To check the specificity of antibody-antigen binding TrkB-IgG (1 μg/ml) as a negative control was used.

Transiently expressed antibody variants were used at 1, 10, and 100 ng/ml.

Detailed procedure as follows:
Coating
Plates: Nunc MaxiSorp 96 well
100 μl/well of TrkA-IgG at 2 μg/ml in Carbonate Buffer 0.1M pH 9.6 (TrkB-IgG used as negative control)
Seal plate and incubate overnight at +4° C.
Wash 3 times with 200 μl of wash buffer
Blocking
Block plates by adding 200 μl of SuperBlock Blocking Buffer in PBS. (Pierce Prod # 37515) to each well.
Immediately empty the plate by inversion.
Repeat two additional times.
Incubate at 37° C. for 2 hours.
Primary Antibody
Discard supernatant and add 1000 of purified mAb appropriately diluted in TEST Buffer (standard curve range: 50-5000 pg/ml).
Seal plate and incubate at 37° C. for 2 hours.
(In order to increase sensitivity incubate overnight at +4° C.)
Wash 4 times with wash buffer.
Secondary Antibody
Add 100 μl of HRP-conjugated Goat anti mouse IgG (Pierce cat. 31430) diluted 1:10000 in TEST Buffer.
Incubate at 37° C. for 1 hour.
Wash 4 times with wash buffer.
Development
Add 100 μl of Substrate solution to each well. Incubate at room temperature. Stop the reaction with 1000 of $H_2SO_4$ 2M.
Determine the optical density of each well using a microtiter reader at 450 nm.

Results

The results for supernatants from the various clones evaluated for antigen binding specificity by using the ELISA assay are shown in FIG. 2.

Briefly, the specific antigen TrkA-IgG (black bars) and the negative control TRKB-IgG (white bars) were coated at 1 μg/ml concentration on different 96-well plates.

Antibodies supernatants were quantified, appropriately diluted, and tested at 5 ng/ml concentration. After washing, binding was detected with the appropriated HRP-labeled secondary antibody, revealed by a chromogenic reaction and quantified by OD450/630 nm measure.

The majority of the humanised antibodies show a comparable selective affinity for high density TrkA antigen.

In addition, their binding specificity is not significantly different from parental murine anti-human TrkA antibody and its chimeric isoform, indicating that antigen selectivity has been fully preserved along the humanisation procedure.

Example 2

Cellular Binding Assay of New Candidates by Cytofluorimetric Analysis of TrkA Surface Expression on TF-1 Cells Procedure
Harvest cells from culture, preparing a single cell suspension.
(In order to obtain maximum antigen expression split cells 1:3 the day before).
Distribute 0.3-0.4×10⁶ cells/sample and wash 1× with cold FACS buffer (PBS pH 7.4+0.1% NaN3+0.1% BSA).
Centrifuge at 350×g for 5 min.
Discard supernatant and Keep tubes on ice.
Fc Receptors Blocking
Add 50 μl/sample of Human IgG [300 μg/ml] in FACS buffer and mix by gently vortexing. Incubate at 4° C. for 15 min.
Primary Antibody
Add 100 μl/sample of Primary Antibody muMNAC13 [4 μg/ml] in FACS buffer and mix by gently vortexing.
As negative control use purified mouse IgG1 isotype control at the same concentration. Incubate at 4° C. for 30 min.
Wash 2× with 1 ml of FACS buffer, spin 5 min at 350×g, and discard the supernatant.

Secondary Antibody

Add 100 μl/sample of Donkey anti Mouse IgG (H+L) R-Phycoerythrin conjugated Jackson ImmunoResearch cat.# 715-116-151 in FACS buffer and mix by gently vortexing.

Incubate at 4° C. for 30 min.

Wash 2× with 1 ml of FACS buffer, spin 5 min at 350×g, and discard the supernatant.

Re-suspend in 0.5 ml of FACS Buffer.

Acquire sample data on flow cytometer.

Results

TF-1 cells were stained with supernatants from all the clones as well as HuMNACWO and HuMNACWOv antibodies as controls (4 μg/ml) for 30 minutes at 4° C.

Staining was revealed by an appropriate PE-labeled secondary antibody and quantified by cytofluorimetric analysis to evaluate the fluorescence intensity of the binding.

The results are shown in FIG. 3, which is based upon the table below.

TABLE 2

| N°. | Variants | Geo Mean Fluorescence Mean ± S.D. | Fold Increase Mean ± S.D. |
|---|---|---|---|
| 1 | mVHEP/mVLEP | 11.0 ± 2.2 | 3.2 ± 0.7 |
| 2 | hVHWOv/hVLWO | 8.9 ± 1.9 | 2.6 ± 0.6 |
| 3 | hVH1/hVL1 | 5.7 ± 0.4 | 1.7 ± 0.1 |
| 4 | hVH1/hVL2 | 4.6 ± 0.4 | 1.3 ± 0.1 |
| 5 | hVH1/hVL3 | 6.1 ± 0.6 | 1.8 ± 0.2 |
| 6 | hVH1/hVL4 | 5.1 ± 0.5 | 1.5 ± 0.2 |
| 7 | hVH1/hVL5 | 4.5 ± 0.3 | 1.3 ± 0.1 |
| 8 | hVH1/hVL6 | 4.9 ± 0.4 | 1.4 ± 0.1 |
| 9 | hVH1/hVL7 | 5.1 ± 0.4 | 1.5 ± 0.1 |
| 10 | hVH1/hVL8 | 5.2 ± 0.1 | 1.5 ± 0.0 |
| 11 | hVH2/hVL1 | 9.2 ± 1.3 | 2.6 ± 0.4 |
| 12 | hVH2/hVL2 | 6.4 ± 0.7 | 1.8 ± 0.2 |
| 13 | hVH2/hVL3 | 10.8 ± 1.3 | 3.1 ± 0.4 |
| 14 | hVH2/hVL4 | 6.1 ± 0.3 | 1.8 ± 0.1 |
| 15 | hVH2/hVL5 | 6.4 ± 0.2 | 1.8 ± 0.1 |
| 16 | hVH2/hVL6 | 6.4 ± 0.7 | 1.8 ± 0.2 |
| 17 | hVH2/hVL7 | 6.5 ± 0.8 | 1.9 ± 0.3 |
| 18 | hVH2/hVL8 | 6.5 ± 1.0 | 1.9 ± 0.3 |
| 19 | hVH3/hVL1 | 8.6 ± 1.5 | 2.5 ± 0.5 |
| 20 | hVH3/hVL2 | 7.1 ± 2.1 | 2.0 ± 0.6 |
| 21 | hVH3/hVL3 | 12.6 ± 0.6 | 3.6 ± 0.2 |
| 22 | hVH3/hVL4 | 7.1 ± 0.1 | 2.0 ± 0.0 |
| 23 | hVH3/hVL5 | 6.9 ± 0.5 | 2.0 ± 0.2 |
| 24 | hVH3/hVL6 | 6.4 ± 0.5 | 1.8 ± 0.2 |
| 25 | hVH3/hVL7 | 7.1 ± 1.0 | 2.0 ± 0.3 |
| 26 | hVH3/hVL8 | 6.5 ± 1.2 | 1.9 ± 0.3 |
| 27 | hVH4/hVL1 | 10.4 ± 2.4 | 3.0 ± 0.7 |
| 28 | hVH4/hVL2 | 8.3 ± 2.5 | 2.4 ± 0.7 |
| 29 | hVH4/hVL3 | 10.9 ± 3.0 | 3.1 ± 0.9 |
| 30 | hVH4/hVL4 | 8.0 ± 2.2 | 2.3 ± 0.6 |
| 31 | hVH4/hVL5 | 8.6 ± 1.7 | 2.5 ± 0.5 |
| 32 | hVH4/hVL6 | 8.0 ± 1.4 | 2.3 ± 0.4 |
| 33 | hVH4/hVL7 | 8.7 ± 2.5 | 2.5 ± 0.7 |
| 34 | hVH4/hVL8 | 8.3 ± 1.9 | 2.4 ± 0.6 |
| 35 | hVH5/hVL1 | 11.3 ± 2.7 | 3.2 ± 0.8 |
| 36 | hVH5/hVL2 | 8.6 ± 2.3 | 2.5 ± 0.7 |
| 37 | hVH5/hVL3 | 13.7 ± 2.1 | 3.9 ± 0.6 |
| 38 | hVH5/hVL4 | 9.1 ± 2.2 | 2.6 ± 0.7 |
| 39 | hVH5/hVL5 | 8.3 ± 2.0 | 2.4 ± 0.6 |
| 40 | hVH5/hVL6 | 9.1 ± 1.5 | 2.6 ± 0.5 |
| 41 | hVH5/hVL7 | 8.6 ± 2.0 | 2.5 ± 0.6 |
| 42 | hVH5/hVL8 | 8.3 ± 1.6 | 2.4 ± 0.5 |
| 43 | huIgG | 3.5 ± 0.0 | 1.0 ± 0.0 |

The results showed that all the clones tested as well as HuMNACWOv positively detected the membrane-associated TrkA receptors on TF1 cells though to a different extent.

HuMNACWO is not able to stain TF1 cells, which have a low density of surface TrkA receptors.

To further confirm, out of 40 clones tested, the best binders were selected to be further analyzed.

As evaluated in two separate experiments (FIG. 4) BXHVH3VL3, BXhVH5VL1, BXhVH5VL3, and HuMNACWOv were compared with HuMNACWO.

The selected leads were confirmed good binders and slightly better performers when compared to HuMNACWOv.

The humanized antibody isoforms BXhVH5VL1 N297A and BXhVH5VL1 together with the reference antibodies muMNACEP and HuMNACWO were also assayed for binding capability on TF-1, HMC-1 and PC12-hTrkA cell lines which express different levels of surface receptor hTrkA.

As shown in FIG. 8, BXhVH5VL1 N297A and BXhVH5VL1 antibodies comparably bind all the tested cell lines, independently of the receptor density on the cellular surface. Both antibodies appear to bind more efficiently when compared to the parental muMNACEP. HuMNACWO only binds high surface receptor density cell line PC12-hTrkA.

Example 3

Comparison of Humanised Antibody Biological Activity In Vitro with a Proliferation Assay on TF1 Cells To measure the ability of anti-human TrkA monoclonal antibodies to block cell surface TrkA-β-NGF mediated biological activity, a cell proliferation assay using a factor-dependent human erythroleukemic cell line, TF-1 (Kitamura, T. et al., 1989, J. Cell Physiol. 140:323-334) was used.

TF-1 cells were incubated with various concentrations of the antibodies for 0.5 hour at 37° C. in a 96 flat well culture plate.

Following this pre-incubation period, recombinant human β-NGF (rec-hu-β-NGF, R&D Systems) was added to the cell-antibody mixture.

The assay mixture in a total volume of 200 μL, containing antibody at different concentrations indicated, human β-NGF at 5.0 ng/mL and TF-1 cells at 5×103 cells/well, was incubated at 37° C. for 5 days in a humidified $CO_2$ incubator.

After that period the plates were centrifuged and, after removal of the supernatant, frozen at −80° C. in order to lyse the cells.

CyQUANT Cell Proliferation Assay Kit (Molecular Probes) was used for measuring cell proliferation according to the manufacturer's instructions.

This experiment was performed twice.

Results

Different humanised candidates were assayed in parallel with murine MNAC13 antibody (muMNACEP), chimNINAC13, HuMNACWO and Human IgG1 as standard control (FIG. 5).

The IC50 were calculated for each curve and the results are given in the table overleaf.

It was found that antibody BXhVH5VL1 was the best performer among the candidates.

The heavy and light chains for this antibody are therefore shown in FIG. 6.

The average IC50 for murine MNAC13 over a series of experiments was 0.54±0.47 μg/ml.

TABLE 3

| Proliferation assay on TF1 cells IC50 (µg/ml) | | |
| --- | --- | --- |
| | Mean | SD |
| muMNACEP | 0.54 | 0.47 |
| | EXP-1 | EXP-2 |
| ChimMNAC13 | 0.06 | 0.58 |
| BXhVH5VL1 | 0.17 | 1.84 |
| BXhVH3VL3 | 0.41 | 2.38 |
| BXhVH5VL3 | 1.40 | 1.21 |
| HuMNACWO | — | — |
| HuIgGstd | — | — |

Example 4

Surface Plasmon Resonance Analysis

Surface plasmon resonance analysis was used to measure the association and dissociation rate constants for binding kinetics of the different antibodies (murine, chimeric, 5 humanised variants) towards TrkA-IgG using BIACORE 2000 (Biacore AB, Uppsala, Sweden). TrkA-IgG was immobilised on a CM-5 sensor chip according to manufacturer's conditions, in a way to achieve an immobilization density of 1100 RU. Each antibody sample was analyzed in antibody concentration ranges of 20-0.63 µg/ml. Calculations from the sensograms were performed by using the BIA evaluation version 3 (1999) software.

Analysis of the individual sets of sensograms was performed with the BIA evaluation version 3 (1999) software. Among the different models tested to fit the kinetics data, the best fitting was obtained with the "separated 1:1" algorithm. In this model, only a defined range of the early association and dissociation curves was used for the calculation. It is assumed that during these early phases of the curve, the overlay effects like mass transfer, rebinding or others do not affect the calculations.

Results

The dissociation constant ($K_D$) was determined for various antibodies and is set out in the table overleaf in the order in order of increasing value.

The $K_D$ value has molar units (M), which correspond to the concentration of ligand at which a binding site on a particular protein is half occupied. The smaller the value, the more tightly bound the ligand, or the higher the affinity between ligand and protein (here between antigen and antibody).

TABLE 4

| Antibody | $K_{on}$ (1/Ms) | $K_{off}$ (1/s) | $K_D$ [M] |
| --- | --- | --- | --- |
| ChimMNAC13 | $2.68 \times 10^5$ | $3.53 \times 10^{-4}$ | $1.51 \times 10^{-10}$ |
| MNAC13 | $8.50 \times 10^5$ | $1.67 \times 10^{-4}$ | $2.50 \times 10^{-10}$ |
| BXhVH5VL1 | $7.68 \times 10^5$ | $4.70 \times 10^{-4}$ | $6.15 \times 10^{-10}$ |
| BXhVH5VL3 | $1.00 \times 10^6$ | $6.38 \times 10^{-4}$ | $6.62 \times 10^{-10}$ |
| BXhVH3VL3 | $3.25 \times 10^5$ | $4.42 \times 10^{-4}$ | $1.45 \times 10^{-9}$ |
| HuMNACWOv | $1.62 \times 10^6$ | $3.86 \times 10^{-3}$ | $2.48 \times 10^{-9}$ |
| HuMNACWO (separate experiment) | $7.39 \times 10^5$ | $3.09 \times 10^{-2}$ | $4.18 \times 10^{-8}$ |

It can be seen from the above table the calculated $K_D$ for the murine and the chimeric isoforms are very comparable with one another.

They are slightly lower but of the same order of magnitude as the humanised variants BXhVH5VL1 and BXhVH5VL3.

On the contrary, the humanised variants HuMNACWOv and BXhVH3VL3 display a one order of magnitude higher $K_D$ than that observed for the murine and the chimeric variants.

However, the $K_D$ values here are still lower than for the prior art humanised antibody HuMNACWO.

Indeed, preferred $K_D$ values for antibodies/variants of the present invention using this model are below $4.18 \times 10^{-8}$ (Thus they are lower than the value for the humanised prior art antibody HuMNACWO).

More preferably they are below $2.48 \times 10^{-9}$ (thus they are lower than for HuMNACWOv, which is a variant of HuMNACWO with the same framework regions, but with changes in the third CDR of the heavy chain).

Most preferably the $K_D$ values are below $1 \times 10^{-9}$ (thus they are of the same general order of magnitude as for the murine and the chimeric isoforms).

Consistently, the ranking given in the above table, which is based on the calculated data using the "separated" algorithm, reflected very well the ranking obtained by visual inspections of the sensograms of all investigated variants in overlay plots.

Example 5

Comparison of Humanised Antibody Biological Activity In Vitro with a Chemokine Secretion Assay on HMC-1 Mast Cell Line NGF acts as an important intermediate in inflammatory pain, contributing to both peripheral and central sensitization. The sensitization of peripheral nociceptors can be very rapid and can involve non-neural cells such as mast cells.

To measure the ability of anti-human TrkA monoclonal antibodies to inhibit β-NGF-induced MIP1α secretion, a biological assay using the mast cell line, HMC-1 (Ahamed, J. et al., J Immunol. 2004 Jun. 1; 172(11):6961-8.) was used.

HMC-1 cells ($0.1 \times 10^6$/well) were plated in triplicate in complete growth medium in a 96 flat well culture plate and incubated with various concentrations of monoclonal antibody for 0.5 hour at 37° C.

Following this pre-incubation period, recombinant human β-NGF (rec-hu-β-NGF, R&D)

Systems) was added to the cell-antibody mixture to a final concentration of 50 ng/ml and incubation at 37° C. was extended for 6 hours in a humidified CO2 incubator.

Supernatants were then harvested and levels of MIP-1β were quantified by sandwich ELISA using a DuoSet® Elisa Kit for Human CCL4/M1-β from R&D System (Cat. Nr. DY271).

Data obtained were expressed as % of response and analyzed with GraphPad Prism 5 software using a nonlinear regression analysis, log(inhibitor) vs. normalized response—variable slope equation.

Results

Figure 9:
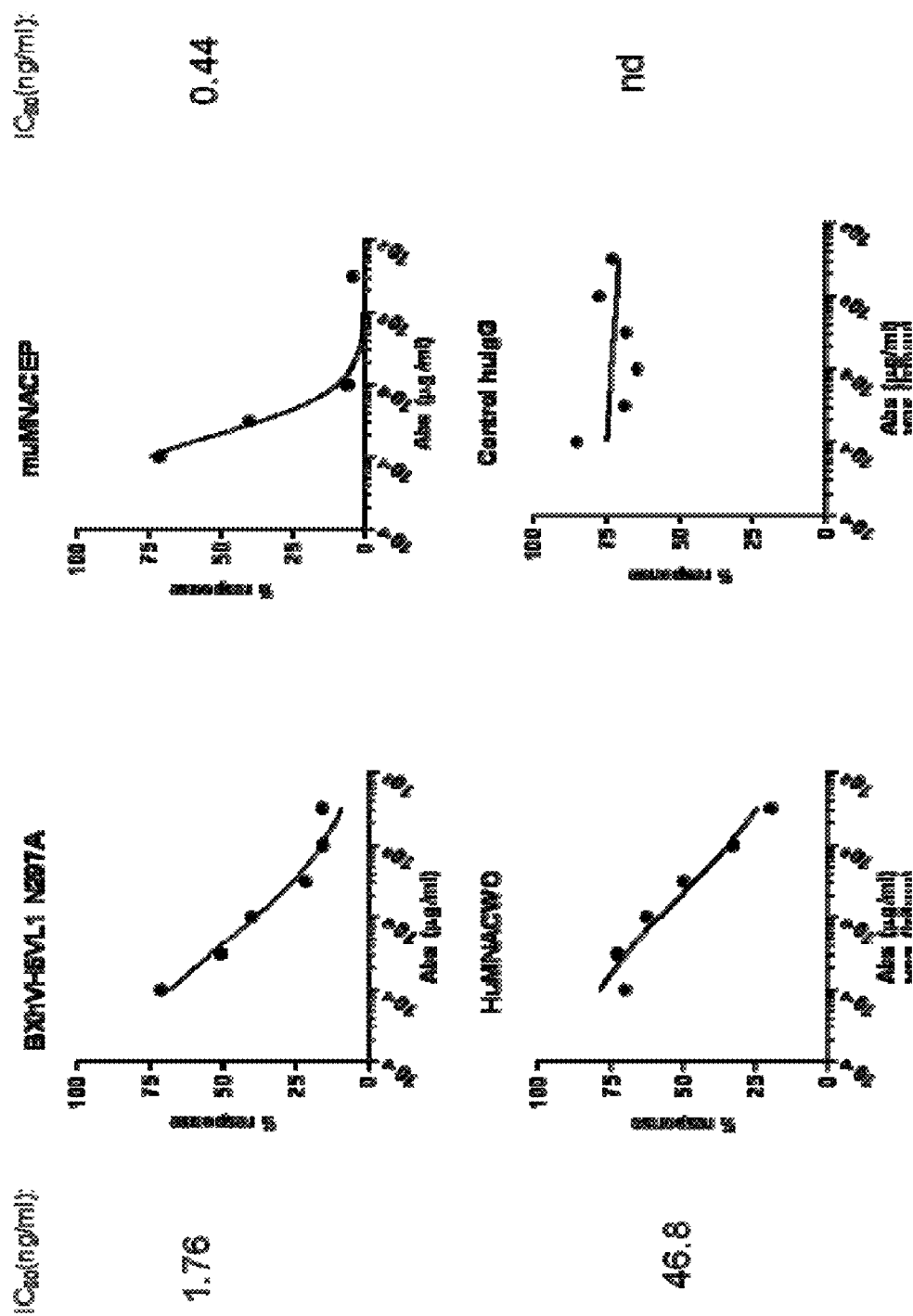
FIG. 9 shows the effect of various antibodies on NGF-induced MIP-1β production in human mast cell line HMC-1.

BXhVH5VL1 N297A antibody was assayed in parallel with murine muMNACEP, HuMNACWO, and Human IgG1 as standard control. The IC50 values were calculated for each curve and the results are shown in FIG. 9. The inhibitory activity of BXhVH5VL1 N297A was significantly higher than that of the humanised antibody HuMNACWO.

Example 6

BXhVH5VL1 N297A and BXhVH5VL1 In Vitro Characterization. Evaluation of Binding to Cellular FcRs on THP-1 Cells Human acute monocytic leukemia cell line THP1 (ATCC) was cultured in RPMI1640/GLUTAMAX (Invitrogen)+10% Foetal Bovine Serum (Invitrogen)+Pen/Strep. and maintained between $2-9 \times 100,000$ cells/ml.

Cells were harvested from culture and prepared as a single cell suspension. $0.3-0.4 \times 10^6$ cells/sample were then distributed in 96-well round-bottom tissue culture plates (Costar, Cambridge, Mass.) and washed 1× with cold FACS buffer.

After centrifugation at 350×g for 5 min., supernatant is discarded and plates put on ice. Binding of IgG to FcγRs on THP-1 cells was performed by incubating monomeric IgGs in FACS Buffer starting from 30 μg/ml to 0.02 μg/ml (dilutions 1:3) in a total volume of 100 μl at 4° C. for 30 min.

Cells were then washed three times with 200 μl of FACS buffer, and IgG binding detection is achieved by adding 100 μl of Donkey anti Human IgG (H+L) R-Phycoerythrin conjugated (Jackson Immuno Research cat.# 709-116-149) 1:100 in FACS buffer. After gentle vortexing, cells were incubated at 4° C. for 30 min.

Plates were washed 2× with 200 μl of FACS buffer, cells are finally resuspended and transferred in 0.5 ml of FACS Buffer and acquired by using a flow cytometer.

Results

Figure 10:
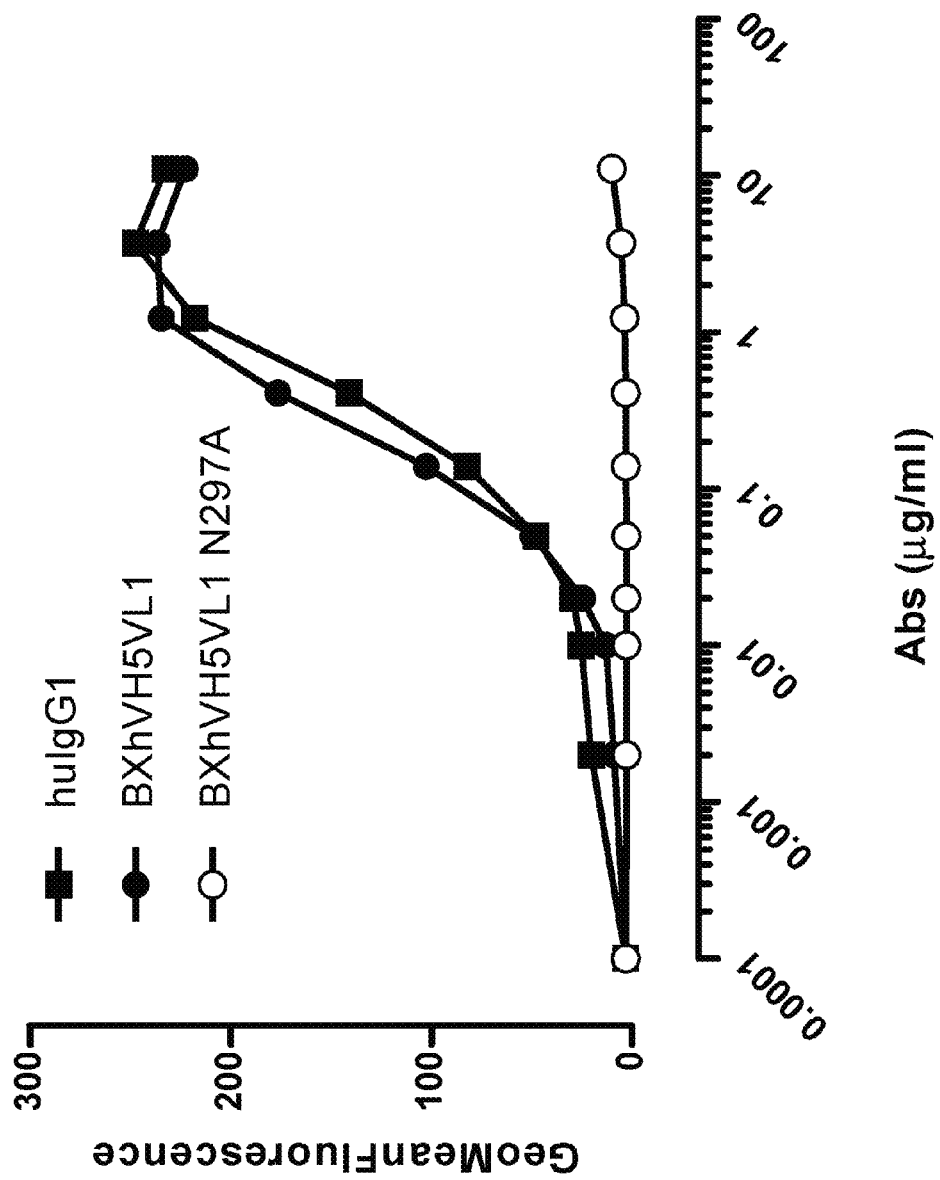
FIG. 10 shows binding of BXhVH5VL1 to cell bound Fc receptors on THP1 cell line compared to BXhVH5VL1 N297A.

FIG. 10 clearly shows that as expected based on prior art disclosures (see U.S. Pat. No. 5,624,821 Winter) the mutated isoform BXhVH5VL1 N297A is devoid of significant binding capability to cellular Fc receptors.

Example 7

In Vivo Experiments

In vivo experiments that were performed to further assay the antibodies/derivatives of the present invention are set out below;

NGF-Mediated Pain Models

Nerve growth factor (NGF) and its receptor TrkA are crucial mediators of the pain sensations characteristic of inflammatory pain.

Classically, NGF is known as a developmental survival factor for sensory and sympathetic neurons but it continues to be synthesized in adult animals in the periphery, where it is transported retrogradely to the cell bodies of sensory neurons (Hendry et al., 1974, Often et al 1980).

Inflammation and nerve injury cause the release of NGF which stimulates primary afferent fibres and induces behavioural sensitisation. Subcutaneous chronic treatment with NGF in rats causes hyperalgesia and alters local cutaneous sensation (Lewin et al., 1993; Andreev et al., 1995).

Intradermal injection of rhNGF into human forearm and masseter muscle in humans causes hyperalgesia, allodynia and alters local cutaneous sensation that began 3 hrs following injection and peaked 1-7 days post injection and recovered by day 21 (Dyck et al., 1997; Svensson et al., 2003).

Thus, injections of rhNGF into the rat hindpaw were used here as a model of behavioural sensitisation that was specifically generated by NGF.

The present experiments involved two different protocols:

1. We first examined whether intradermal injection of recombinant human (rh) NGF alone in rat paw could cause behavioural sensitisation as measured by standard nociceptive tests for hyperalgesia (Hargreave's plantar test). We then established whether intradermal co-injection of the murine IgG, muMNACEP, human IgG, and BXhVH5VL1 N297A antibodies at a dose of 100 μg could affect the rhNGF-induced sensitisation. Murine $IgG_1$ and human IgG antibodies ware used as a negative controls at the appropriated dosages.

2. We then established whether systemic pre-treatment of muMNACEP antibody (at doses of 8 and 1 mg/Kg, i.p.) and BXhVH5VL1 N297A (doses of 8, 3, and 1 mg/Kg, i.p.) could affect the peripherally induced rhNGF sensitisation.

In the first protocol, whereby treatments where administered locally, male Lewis rats (Charles River, 5-6 weeks 200 g) were used with 8-9 animals per group and 4 experimental groups, injected according to the set method. Injections were carried out blind. A summary of the treatments is outlined in the table below.

|  | muMNACEP/ BXhVH5VL1 N297A | $mIgG_1$/hIgG |
|---|---|---|
| Intradermal treatments | 100 μg + 500 ng rhNGF, n = 9 | 100 μg + 500 ng rhNGF, n = 9 |

In the second protocol, whereby treatments were administered systemically (i.p.) 24 hrs prior to rhNGF paw injection, male Lewis rats (Charles River, 5-6 weeks 200 g) were used with 10-12 animals per group and 10 experimental groups. Injections were carried out blind. A summary of the treatments is outlined in the table below.

|  | muMNACEP | $mIgG_1$ | BXhVH5VL1 N297A | hIgG |
|---|---|---|---|---|
| Systemic i.p. 24 hr pre-treatments | 1 mg/Kg n = 10 8 mg/Kg n = 10 | 1 mg/Kg n = 12 8 mg/Kg n = 8 | 1 mg/Kg n = 10 3 mg/Kg n = 10 8 mg/Kg n = 12 | 1 mg/Kg n = 10 3 mg/Kg n = 10 8 mg/Kg n = 12 |
| rhNGF intradermal | 500 ng | 500 ng | 500 ng | 500 ng |

Assay

All animals were numbered and then habituated to behaviour-testing procedures 24-48 hr prior to commencement of the experiment. Behaviour readouts were the paw withdrawal latency to the plantar test as a measure of hyperalgesia.

Baseline recordings were taken to establish paw withdrawal latencies. Nociceptive sensitivity was induced by intradermal rhNGF injected at Time point 0 and behavioural nociceptive sensitivity was monitored 30 minutes, 1 hour, 2 hours, 24 hours and 48 hours following rhNGF injection. Treatments were administered blind as follows:

Protocol 1: Treatment administration by intradermal injection at Time 0.

Protocol 2: Treatment administration by systemic single injection IP 24 h before rhNGF paw injection.

Baseline plantar and von Frey tests were performed before drug treatments were administered.

Hyperalgesia measurements were taken 30 min, 1 hr, 2 hrs, 24 hrs and 48 hrs after rhNGF injection. Three to four recordings were taken for each hindpaw ipsilateral (right paw, rhNGF-injected) and contralateral (left paw, un-injected) to rhNGF injection.

Data from animals from individual treatment groups were collated, and means and standard deviations were calculated for the controlateral and ipsilateral paw responses.

The presence of hyperalgesia was indicated by a significant reduction in the paw withdrawal latency (recorded in seconds) in the rhNGF-injected ipsilateral hindpaw when compared with the control contralateral paw (by paired t-test) and when compared with the pre-injection/pre-treatment baseline (by one-way ANOVA).

Intradermal Anti-Hyperalgesic Efficacy

We compared the anti-hyperalgesic efficacy of BXhVH5VL1 N297A (FIG. 11) and muMNACEP (FIG. 12) (plus mIgG$_1$ and hIgG as relative controls) by intradermal injection in this model of NGF-induced hyperalgesia.

When BXhVH5VL1 N297A and muMNACEP were co-injected with rhNGF, there was no significant development of hyperalgesia, as indicated by no significant difference between ipsilateral and contralateral paw withdrawal responses (FIGS. 11 and 12).

Hyperalgesia in ipsilateral paw responses were always present following co-injection with the negative controls (mIgG$_1$, hIgG).

Data are represented as means±95% CI, before (baseline) and following intradermal injection of 500 ng rhNGF with respective treatments (at arrow). Significant reduction in paw withdrawal latency ipsilateral is indicated by '*' '**' ($p<0.05$, $p<0.01$, paired t-test) when compared to the contralateral paw withdrawal.

Systemic Anti-Hyperalgesic Efficacy

We compared the anti-hyperalgesic efficacy of BXhVH5VL1 N297A, muMNACEP mIgG1, and hIgG by systemic injection in this model of NGF-induced hyperalgesia.

Figure 13:
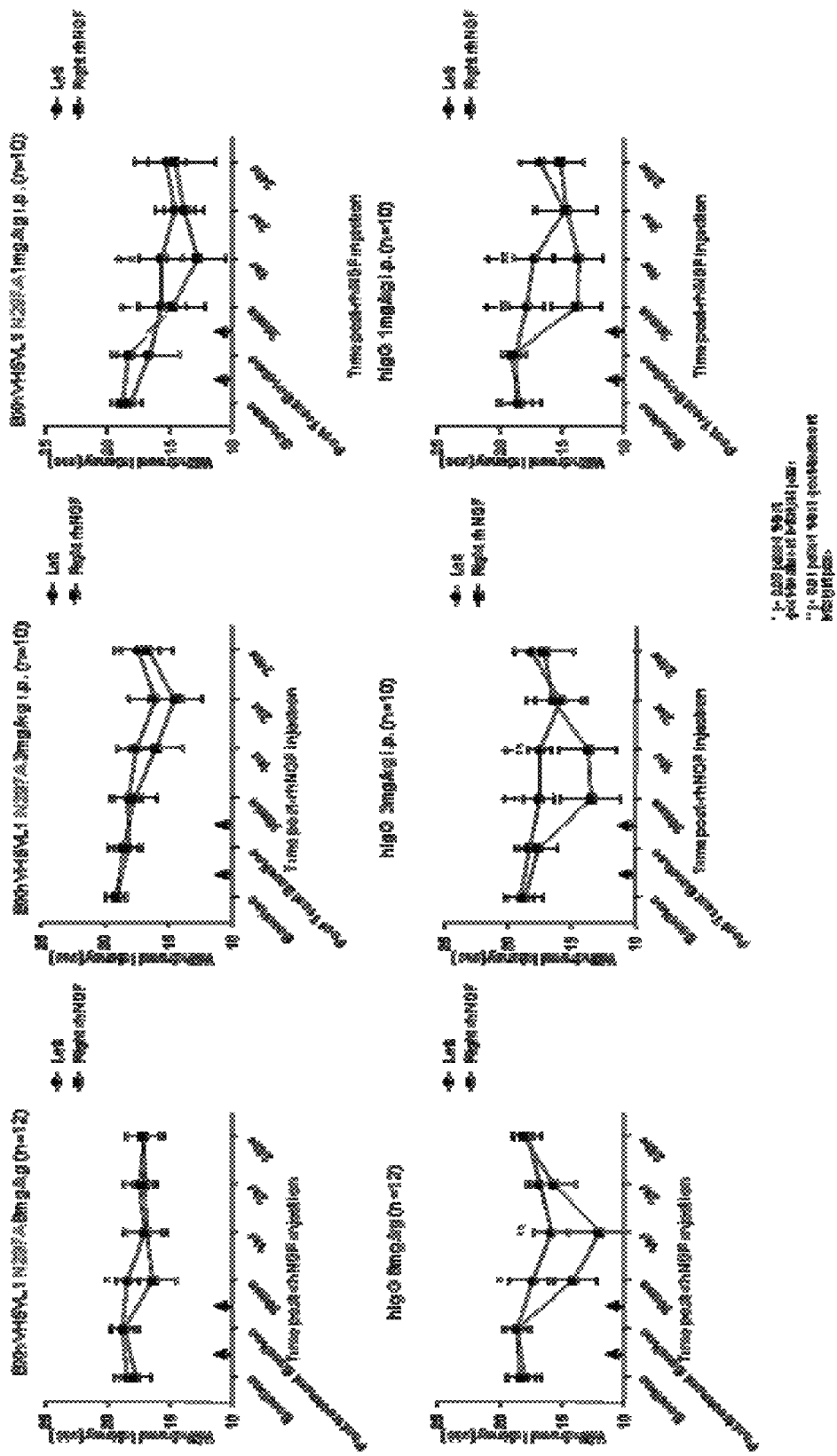
FIG. 13 shows an experiment demonstrating the analgesic effect of systemic administration of BXhVH5VL1 N297A when compared to control hIgG in an animal model of NGF-induced pain.
Figure 14:
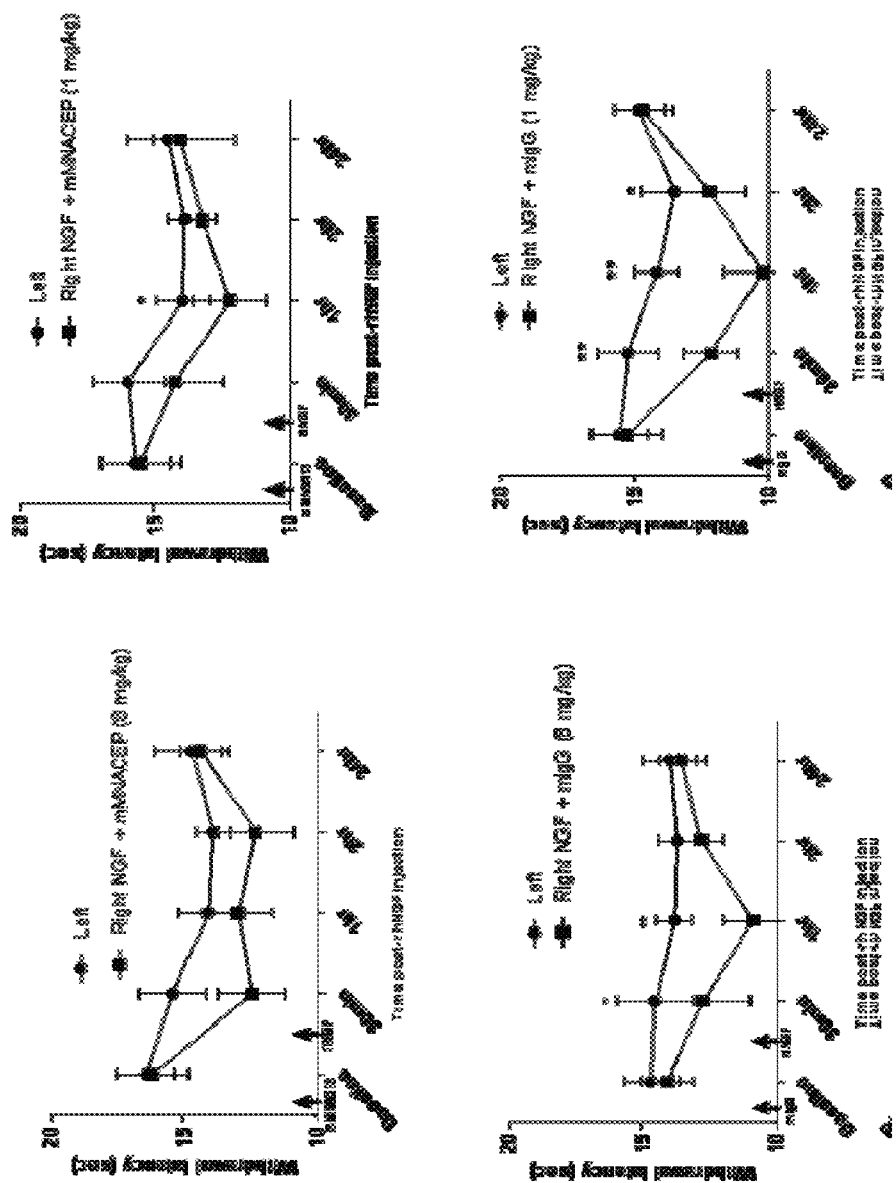
FIG. 14 shows an experiment demonstrating the analgesic effect of systemic administration of muMNACEP when compared to control hIgG in an animal model of NGF-induced pain.

Three different doses of BXhVH5VL1 N297A and control hIgG (1, 3, and 8 mg/Kg) were tested (FIG. 13). Similarly, two different doses of muMNACEP and mIgG1 were tested, 1 mg/Kg and 8 mg/Kg (FIG. 14). All treatments were administered i.p. 24 hours prior to intradermal injection with rhNGF.

Systemic pre-treatment of 8 and 3 mg/kg BXhVH5VL1 N297A significantly prevented the development of hyperalgesia following rhNGF injection, as indicated by no significant difference between ipsilateral and contralateral paw withdrawal responses (FIG. 13).

Systemic pre-treatment with the murine parental antibody mMNACEP (8 mg/Kg) also prevented the development of rhNGF-induced hyperalgesia (FIG. 14). However, the overall analgesic response of BXhVH5VL1 N297A appeared to be better as compared with mMNACEP antibody.

At the same dose, hyperalgesia in ipsilateral paw responses was always present following co-injection with the negative control mIgG$_1$ and hIgG.

Data are represented as means±95% CI, before (baseline) and following intradermal injection of 500 ng rhNGF with respective treatments (at arrow). Significant reduction in paw withdrawal latency ipsilateral is indicated by '*' '**' ($p<0.05$, $p<0.01$, paired t-test) when compared to the contralateral paw withdrawal.

Example 8

Further in vivo experiments that may be performed to further assay the antibodies/derivatives of the present invention are set out below:

Formalin Test

Mice are pretreated with the antibody/derivative intraperitoneally and 18 hours later are injected in the right dorsal footpad with 5% Formalin. Licking time (time spent licking the injured paw) is measured for up to 1 hour.

Chronic Constriction Injury Test

Mice are subject to surgical constriction of sciatic nerve, in order to induce a neuropathic allodynia. Animals are then treated with antibody/derivative and withdrawal response to a mechanical stimulus localized to the injured limb versus the contralateral limb is measured.

Arthritis Model

Rats are injected with complete Freund's adjuvant at the tail base intradermally. Approximately three weeks late they develop a systemic poly arthritis characterized by joint pain. Animals are treated with the antibody/derivative and the analgesic effect is evaluated by the vocalization assay consisting of measurement of intensity of vocalization upon gentle manipulation of the joints.

Monkey Carrageenan Induced Pain Model

Rhesus macaques are pretreated intravenously with the antibody/derivative. The following day, animals are injected subcutaneously with carrageenan in the tail. Withdrawal time from a heat stimulus is measured.

General Points

Unless the context indicates otherwise, the following general points apply:

1) All references discussed herein are deemed to be incorporated by reference.

2) The term "comprises" is non-limiting in that it covers "including" as well as "consisting of". Thus the word 'comprises' and variations such as 'comprise' and 'comprising' will be understood to imply the inclusion of a stated integer, step, group of integers or group of steps but not to the exclusion of any other integer, step, group of integers or group of steps.

3) Equivalents of aspects of the invention discussed herein are considered to be within the scope of the invention, even if the equivalents are not specifically discussed.

The invention claimed is:

1. An anti-TrkA antibody comprising:
   a) a variable heavy chain consisting of the sequence BXhVH5 (SEQ ID NO: 5); and
   b) a variable light chain consisting of the sequence BXhVL1(SEQ ID NO: 7);
   or an antigen binding fragment thereof.

2. The antibody of claim 1 that is PEGylated.

3. The antibody of claim 1 in immobilised form.

4. The antibody of claim 1 for use in medicine.

5. A method for the treatment of pain, said method comprising:
   administering to a subject the antibody of claim 1.

6. The method of claim 5, wherein the pain is chronic pain.

7. The method of claim 5, wherein the pain is acute pain.

8. A combination of the antibody of claim 1 and an analgesic, for simultaneous, sequential or concerted administration in medicine.

9. A combination of the antibody of claim 1 and NGF, for simultaneous, sequential or concerted administration in medicine.

10. A combination of the antibody of claim 1 and a further anti-TrkA antibody or derivative thereof, for simultaneous, sequential or concerted administration in medicine.

11. A pharmaceutical composition comprising the antibody of claim 1 and a pharmaceutically acceptable carrier or excipient.

12. A pharmaceutical composition comprising the antibody of claim 1 and another pharmaceutically active agent.

13. The pharmaceutical composition of claim 12; wherein said another agent is one or more of:
   a) an analgesic agent
   b) another anti-TrkA antibody or derivative thereof
   c) NGF
   d) an anti-cancer agent.

14. The antibody of claim 1 for use in diagnosis or prognosis.

15. The antibody of claim 1 for use in the diagnosis or prognosis of a condition involving aberrant expression of TrkA or an aberrant activity involving TrkA.

16. An antibody or antigen binding fragment thereof according to claim 1 for use in the diagnosis or prognosis of any of the diseases or disorders selected from the group consisting of: chronic pain and acute pain.

17. A method comprising obtaining a biological sample and contacting the sample to detect binding of an antibody or antigen binding fragment thereof according to claim 1 thereto.

18. A method according to claim 17 further comprising comparing the results for binding of said antibody or antigen binding fragment thereof to said sample with a positive or negative control sample.

19. A non-human transgenic mammal that expresses the antibody of claim 1 or that can be induced to provide such expression.

20. A kit of parts comprising the antibody of claim 1 together with instructions directing the use thereof by a subject as an analgesic.

* * * * *